(12) United States Patent
Plahey

(10) Patent No.: US 11,759,560 B2
(45) Date of Patent: Sep. 19, 2023

(54) SAFETY MECHANISM FOR A DIALYSIS SYSTEM

(71) Applicant: Fresenius Medical Care Holdings, Inc., Waltham, MA (US)

(72) Inventor: Kulwinder Plahey, Concord, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 279 days.

(21) Appl. No.: 17/021,857

(22) Filed: Sep. 15, 2020

(65) Prior Publication Data
US 2022/0080092 A1    Mar. 17, 2022

(51) Int. Cl.
*A61M 1/28*    (2006.01)
*A61M 60/40*    (2021.01)
*A61M 39/24*    (2006.01)
*A61M 39/28*    (2006.01)

(52) U.S. Cl.
CPC ............ *A61M 1/282* (2014.02); *A61M 39/24* (2013.01); *A61M 39/28* (2013.01); *A61M 60/40* (2021.01); *A61M 2205/12* (2013.01); *A61M 2205/273* (2013.01); *A61M 2205/3337* (2013.01); *A61M 2205/3553* (2013.01); *A61M 2205/3561* (2013.01)

(58) Field of Classification Search
CPC .................................. A61M 1/14; A61M 1/28
See application file for complete search history.

(56) References Cited

U.S. PATENT DOCUMENTS

| 4,033,379 | A | | 7/1977 | Tooley |
| 4,585,436 | A | * | 4/1986 | Davis ................. A61M 1/1643 604/83 |
| 5,350,357 | A | | 9/1994 | Kamen et al. |
| 5,472,420 | A | * | 12/1995 | Campbell ............ A61M 5/148 604/67 |

(Continued)

FOREIGN PATENT DOCUMENTS

| JP | 2006/181386 A | 7/2006 |
| WO | WO 2013/095459 A9 | 6/2013 |

OTHER PUBLICATIONS

International Patent Application No. PCT/US2021/046790, International Search Report (Nov. 22, 2021).

*Primary Examiner* — Courtney B Fredrickson
(74) *Attorney, Agent, or Firm* — Leydig, Voit & Mayer, Ltd.

(57) ABSTRACT

A dialysis machine (e.g., a peritoneal dialysis (PD) machine) can include a safety feature that is used to isolate individual fluid lines attached to a disposable cassette. The PD machine can include an interface for a disposable cassette, a plurality of safety mechanisms, and a processor. A plurality of fluid lines are connected to the disposable cassette, and each safety mechanism corresponds to a particular fluid line in the plurality of fluid lines. The processor is configured to detect a hazard condition, such as a loss of power to the PD machine or leak in the disposable cassette, and activate one or more safety mechanisms to isolate corresponding fluid lines connected to the disposable cassette. In one embodiment, the safety mechanisms are spring-loaded clamping mechanisms configured to compress a distensible tube connected to the fluid line. In another embodiment, the safety mechanisms include relay solenoids and/or check valves.

12 Claims, 16 Drawing Sheets

(56) References Cited

U.S. PATENT DOCUMENTS

| | | |
|---|---|---|
| 2003/0217962 A1 | 11/2003 | Childers et al. |
| 2003/0220598 A1 | 11/2003 | Busby et al. |
| 2004/0019313 A1 | 1/2004 | Childers et al. |
| 2005/0230292 A1 | 10/2005 | Beden et al. |
| 2007/0125709 A1 | 6/2007 | Nigam |
| 2008/0015493 A1* | 1/2008 | Childers ............. A61M 1/3458 604/29 |
| 2009/0009290 A1 | 1/2009 | Kneip et al. |
| 2009/0107902 A1* | 4/2009 | Childers ............. A61M 1/1621 210/321.71 |
| 2011/0184340 A1* | 7/2011 | Tan .................... B01J 20/06 604/29 |
| 2014/0319035 A1 | 10/2014 | Burbank et al. |

\* cited by examiner

SAFETY MECHANISM FOR A DIALYSIS SYSTEM

BACKGROUND

Dialysis is a treatment used to support a patient with insufficient renal function. The two principal treatment options are hemodialysis (HD) and peritoneal dialysis (PD). During hemodialysis, the patient's blood is removed, e.g., via an arteriovenous (AV) fistula or other methods (e.g., AV graft), and passed through a dialyzer of a dialysis machine while also passing a dialysis solution, referred to as dialysate, through the dialyzer. A semi-permeable membrane in the dialyzer separates the blood from the dialysate within the dialyzer and facilitates the exchange of waste products (e.g., urea, creatine, potassium, etc.) between the blood stream and the dialysate. The membrane prevents the transfer of blood cells, protein, and other important components in the blood stream from entering the dialysate solution. The cleaned blood stream is then returned to the patient's body. In this way, the dialysis machine functions as an artificial kidney for cleaning the blood in patients with insufficient renal function.

In contrast with hemodialysis, the peritoneal dialysis treatment option introduces dialysate into a patient's peritoneal cavity, which is an area in the abdomen between the parietal peritoneum and visceral peritoneum (e.g., a space between the membrane that surrounds the abdominal wall and the membranes that surround the internal organs in the abdomen). The lining of the patient's peritoneum functions as a semi-permeable membrane that facilitates the exchange of waste product between the bloodstream and the dialysate, similar in function to the membrane in the dialyzer of the hemodialysis machine. The patient's peritoneal cavity is drained and filled with new dialysate over a number of PD cycles. Peritoneal dialysis can be performed using either gravity or an automated pumping mechanism to fill and drain the abdomen during a PD cycle.

Automated PD machines, sometimes referred to as PD cyclers, are designed to control the PD treatment process so that it can be performed at home without clinical staff, typically while the patient sleeps overnight so as to minimize interference with the patient's life. The process is referred to as continuous cycler-assisted peritoneal dialysis (CCPD). Many PD cyclers are designed to automatically infuse, dwell, and drain dialysate to and from the peritoneal cavity. The PD treatment typically lasts several hours, often beginning with an initial drain phase to empty the peritoneal cavity of used or spent dialysate that was left in the peritoneal cavity at the end of the last PD treatment. The sequence then proceeds through a progression of fill, dwell, and drain phases that follow sequentially. A group of fill, dwell, and drain phases, in order, can be referred to as a PD cycle.

Automated PD machines conventionally use a pump to both fill and drain the patient. However, in some cases, a failure can occur with certain components attached to the PD machine. For example, a line (e.g., a distensible tube) can rupture or a connection between a line and a dialysate bag can leak or break. In some cases, a pump failure in the PD machine can lead to uncontrolled fluid flow (e.g., backflow), and can lead to cases such as overfilling the patient's abdominal cavity, a loss of dialysate, and the like. When the PD machine is not functioning normally due to such issues, then there can be a chance that contaminated fluid (e.g., spent dialysate) could be directed somewhere other than the drain, which could require cleanup of biohazardous material or could contaminate clean dialysate attached to the PD machine. It is desirable to include a safety mechanism in automated PD machines that enables all lines attached to a cassette to be isolated from the cassette to prevent flow of any fluid contained therein to the other lines.

Existing safety mechanisms use a clamp that can shut off all lines (e.g., 8-10 lines) at once when a spring loaded mechanism is released. However, these safety mechanisms are bulky due to the high amount of force required to clamp all the lines at once. For example, the high force may require larger springs, a thicker structural member for the clamping mechanism, and so forth. Such requirements increase the size and cost of PD machines that implement such safety mechanisms. Thus, there is a desire to implement new safety mechanisms that provide similar features while reducing the size or the cost of the PD machine.

SUMMARY

In accordance with one aspect of the disclosure, a dialysis system is provided that includes a safety feature. The dialysis system can include an interface for a disposable cassette, a plurality of safety mechanisms, and a processor. A plurality of fluid lines are connected to the disposable cassette, and each safety mechanism corresponds to a particular fluid line in the plurality of fluid lines. The processor is configured to detect a hazard condition and activate one or more safety mechanisms to isolate corresponding fluid lines connected to the disposable cassette.

In one embodiment, the safety mechanisms are spring-loaded clamping mechanisms configured to compress a distensible tube connected to the fluid line. In another embodiment, the safety mechanisms include relay solenoids and/or check valves.

In an embodiment, each safety mechanism operates to clamp a distensible tube of the particular fluid line to close a fluid pathway in the distensible tube. In another embodiment, each safety mechanism comprises a relay solenoid.

In an embodiment, at least two safety mechanisms are activated by a single actuator connected to the at least two safety mechanisms. In some embodiments, the actuator comprises a motor connected to a shaft that rotates a plurality of sear components.

In an embodiment, the hazard condition is a loss of power. In another embodiment, detecting the hazard condition comprises monitoring a user interface to detect manual selection of a control element of the user interface associated with each of the one or more safety mechanisms.

In an embodiment, the plurality of safety mechanisms are included in a safety module communicatively coupled to a dialysis machine via a wired or a wireless communications interface.

In an embodiment, at least one safety mechanism includes a check valve. In some embodiments, a safety mechanism includes a spring-loaded clamping mechanism and a check valve.

In an embodiment, each safety mechanism can be automatically reset by the dialysis system. In some embodiments, an actuator is attached to a compression member to retract the compression member into an opening in the interface for the cassette, upon retraction, the sear component locks the compression member in the retracted state. In another embodiment, each safety mechanism is manually reset by pushing the compression member into the opening.

In accordance with another aspect of the disclosure, a method of operating a dialysis machine is disclosed. The method includes: detecting a hazard condition; and activating one or more safety mechanisms in a plurality of safety mechanisms to isolate corresponding fluid lines connected to a disposable cassette. A plurality of fluid lines are connected to the disposable cassette, and each safety mechanism corresponds to a particular fluid line in the plurality of fluid lines.

In an embodiment, activating the one or more safety mechanisms comprises transmitting a signal to the safety module via the communications interface.

In accordance with another aspect of the disclosure, a non-transitory computer readable storage medium is provided. The computer readable storage medium stores instructions that, when executed by a processor, causes a dialysis machine to perform steps comprising: detecting a hazard condition; and activating one or more safety mechanisms in a plurality of safety mechanisms to isolate corresponding fluid lines connected to a disposable cassette. A plurality of fluid lines are connected to the disposable cassette, and each safety mechanism corresponds to a particular fluid line in the plurality of fluid lines.

DETAILED DESCRIPTION

A dialysis machine, such as a peritoneal dialysis (PD) machine, can be designed to include a safety feature. The safety feature operates to isolate fluid lines connected to a disposable cassette when a hazard condition is detected. For example, when the PD machine loses power, the safety feature can be activated to ensure that no fluid flows between the patient and the cassette. Different hazard conditions, monitored through different sensors of the PD machine, can trip the safety feature. In addition, the safety mechanisms can be manually operated through a user interface of the PD machine.

In some embodiments, the PD machine includes multiple safety mechanisms, with each fluid line corresponding to a separate and distinct safety mechanism. This allows for fluid lines to be isolated individually. Another benefit for having individual safety mechanisms is that the force required to implement the safety feature for a single fluid line can be less than a force required to implement the safety feature for all of the fluid lines as a group. By reducing the force required for each safety mechanism, the components of the safety mechanism may be smaller and easier to incorporate into the physical envelope of existing designs of PD machines.

The safety mechanisms can be implemented to clamp a distensible tube associated with a fluid line in order to compress the walls of the distensible tube to obstruct a fluid path therein. In other embodiments, the safety mechanism can incorporate check valves and/or relay solenoids to shut off the fluid path, either in addition to or in lieu of the clamping mechanism.

In some cases, the safety feature is incorporated into an existing PD machine. In other cases, the safety feature can be implemented as an auxiliary module that can be added to legacy PD machines without the safety feature.

Figure 1:
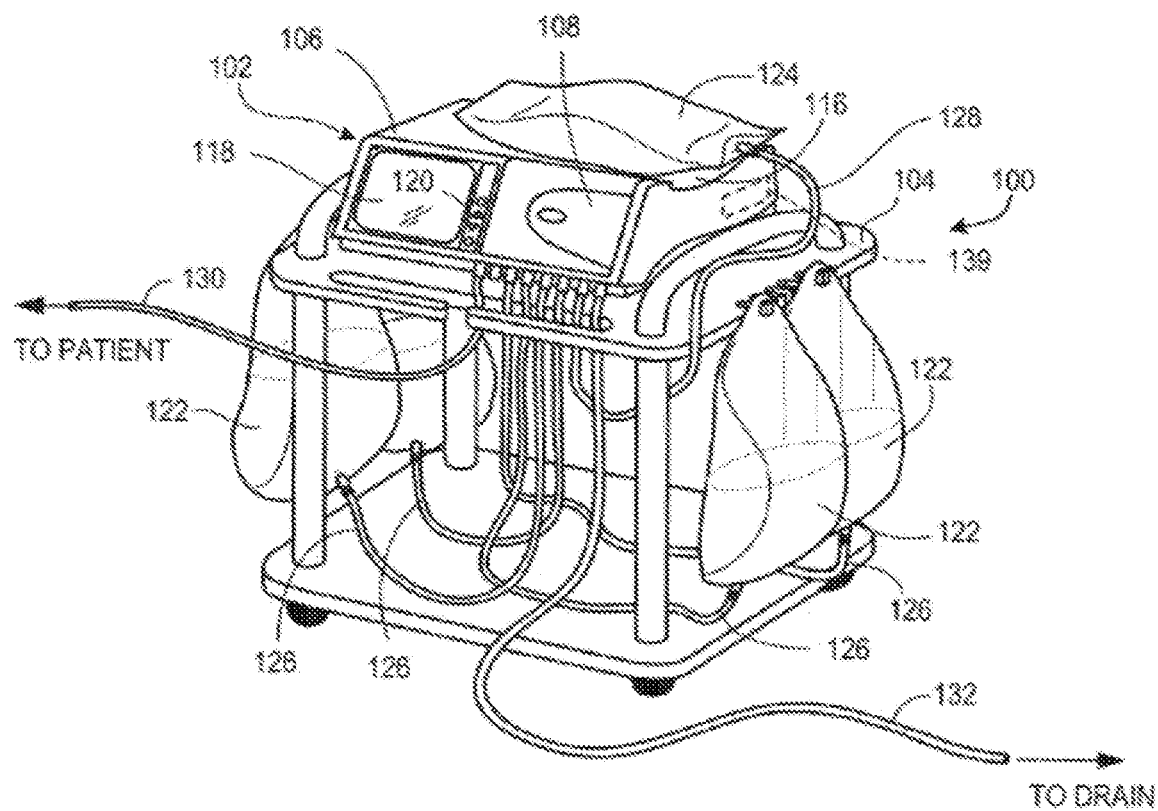
FIG. 1 illustrates a peritoneal dialysis (PD) system, in accordance with some embodiments.

FIG. 1 illustrates a peritoneal dialysis (PD) system 100, in accordance with some embodiments. The PD system 100 can include a PD machine 102, which can alternately be referred to as a PD cycler, seated on a cart 104. The PD machine 102 includes a housing 106, a door 108, and a cassette interface 110 that contacts a disposable PD cassette 112 when the cassette 112 is disposed within a cassette compartment 114 formed between the cassette interface 110 and the closed door 108. The cassette compartment 114, cassette interface 110, and cassette 112 are shown in more detail in FIG. 2. A heater tray 116 is positioned on top of the housing 106. The heater tray 116 is sized and shaped to accommodate a bag of PD solution such as dialysate (e.g., a 5 liter bag of dialysate). The PD machine 102 also includes a user interface such as a touch screen display 118 and additional control buttons 120 that can be operated by a user (e.g., a caregiver or a patient) to allow, for example, set up, initiation, and/or termination of a PD treatment.

Dialysate bags 122 are suspended from fingers on the sides of the cart 104, and a heater bag 124 is positioned in the heater tray 116. The dialysate bags 122 and the heater bags 124 are connected to the cassette 112 via dialysate bag lines 126 and a heater bag line 128, respectively. The dialysate bag lines 126 can be used to pass dialysate from dialysate bags 122 to the cassette 112 during use, and the heater bag line 128 can be used to pass dialysate back and forth between the cassette 112 and the heater bag 124 during use. In addition, a patient line 130 and a drain line 132 are connected to the cassette 112. The patient line 130 can be connected to a patient's abdomen via a catheter and can be used to pass dialysate back and forth between the cassette 112 and the patient's peritoneal cavity during use. The catheter may be surgically implanted in the patient and connected to the patient line 130 via a port, such as a fitting, prior to the PD treatment. The drain line 132 can be connected to a drain or drain receptacle and can be used to pass dialysate from the cassette 112 to the drain or drain receptacle during use.

The PD machine 102 also includes a control unit 139 (e.g., a processor, controller, system-on-chip (SoC), or the like). The control unit 139 can receive signals from and transmit signals to the touch screen display 118, the control panel 120, and the various other components of the PD system 100. The control unit 139 can control the operating parameters of the PD machine 102. In some embodiments, the control unit 139 includes an MPC823 PowerPC device manufactured by Motorola, Inc. As further discussed in detail elsewhere herein, in some embodiments, the control unit 139 may be configured to control disengaging and/or bypassing of a pump in connection with naturally draining the dialysate from a patient during the drain phase of a PD cycle.

Figure 2:
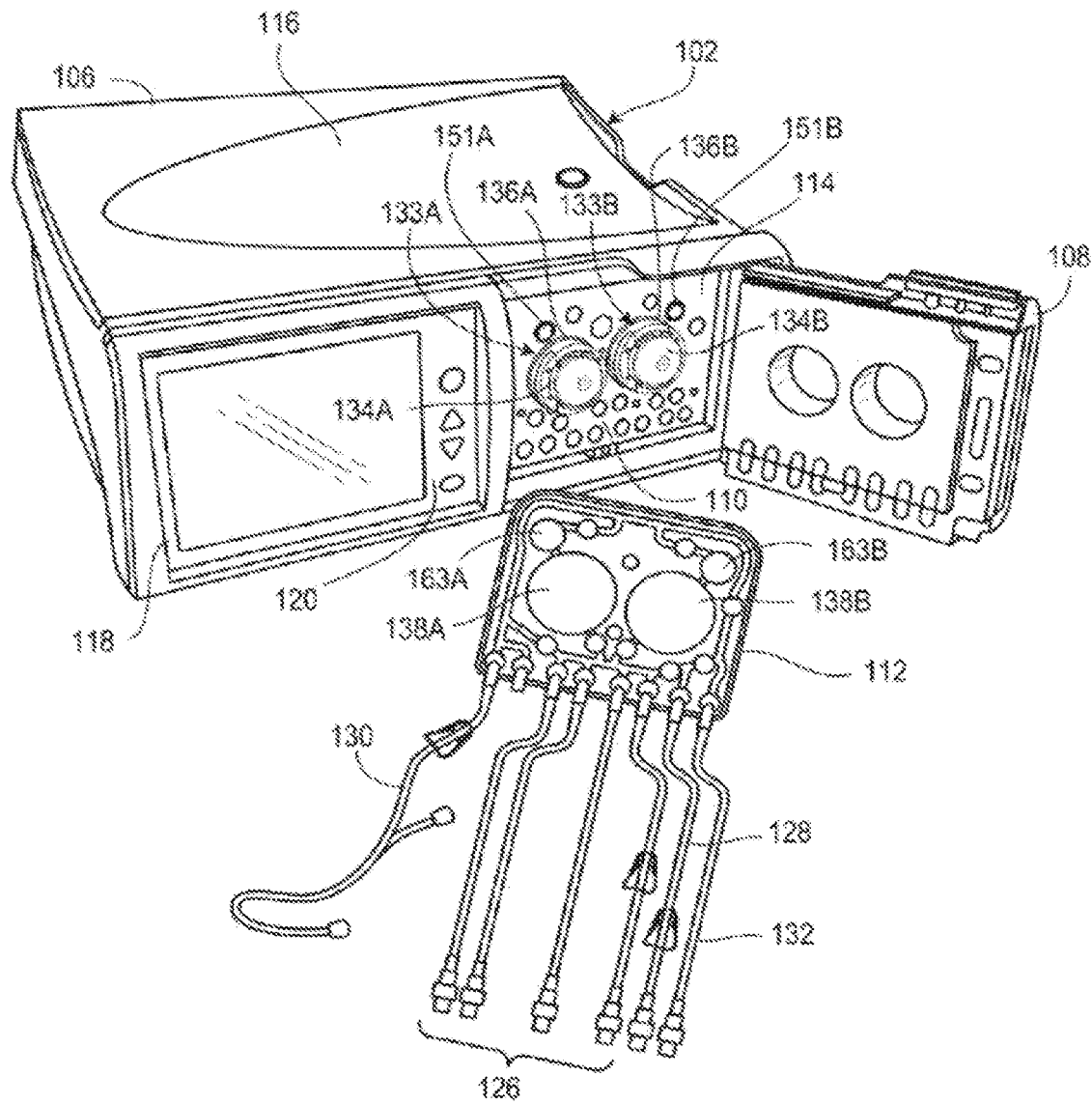
FIG. 2 is a perspective view of the PD machine and the PD cassette of the PD system of FIG. 1, in accordance with some embodiments

FIG. 2 is a perspective view of the PD machine 102 and the PD cassette 112 of the PD system 100 of FIG. 1, in accordance with some embodiments. As depicted in FIG. 2, the PD cassette 112 is placed proximate the cassette interface 110. The cassette 112 contains pump chambers 138A, 138B, pressure sensing chambers 163A, 163B, and valve chambers for controlling the flow of fluid through the cavities of the cassette 112. The cassette 112 is connected to the dialysate bag lines 126, the heater bag line 128, the patient line 130, and the drain line 132.

The cassette interface 110 includes a surface having holes formed therein. The PD machine 102 includes pistons 133A, 133B with piston heads 134A, 134B attached to piston shafts. The piston shafts can be actuated to move the piston heads 133A, 133B axially within piston access ports 136A, 136B formed in the cassette interface 110. The pistons 133A, 133B are sometimes referred to herein as pumps. In some embodiments, the piston shafts can be connected to stepper motors that can be operated to move the pistons 133A, 133B axially inward and outward such that the piston heads 134A, 134B move axially inward and outward within the piston access ports 136A, 136B. The stepper motors drive lead screws, which move nuts inward and outward on the lead screws. The stepper motors can be controlled by driver modules. The nuts, in turn, are connected to the piston shafts, which cause the piston heads 134A, 134B to move axially inward and outward as the stepper motors drive the lead screws. Stepper motor controllers provide the necessary current to be driven through the windings of the stepper motors to move the pistons 133A, 133B. The polarity of the current determines whether the pistons 133A, 133B are advanced or retracted. In some embodiments, the stepper motors require 200 steps to make a full rotation, and this corresponds to 0.048 inches of linear travel of the piston heads 134A, 134B.

In some embodiments, the PD system 100 also includes encoders (e.g., optical quadrature encoders) that measure the rotational movement and direction of the lead screws. The axial positions of the pistons 133A, 133B can be determined based on the rotational movement of the lead screws, as indicated by feedback signals from the encoders. Thus, measurements of the position calculated based on the feedback signals can be used to track the position of the piston heads 134A, 134B of the pistons 133A, 133B.

When the cassette 112 is positioned within the cassette compartment 114 of the PD machine 102 with the door 108 closed, the piston heads 134A, 134B of the PD machine 102 align with the pump chambers 138A, 138B of the cassette 112 such that the piston heads 134A, 134B can be mechanically connected to dome-shaped fastening members of the cassette 112 overlying the pump chambers 138A, 138B. As a result of this arrangement, movement of the piston heads 134A, 134B toward the cassette 112 during treatment can decrease the volume of the pump chambers 138A, 138B and force dialysate out of the pump chambers 138A, 138B. Retraction of the piston heads 134A, 134B away from the cassette 112 can increase the volume of the pump chambers 138A, 138B and cause dialysate to be drawn into the pump chambers 138A, 138B.

The cassette 112 also includes pressure sensor chambers 163A, 163B. When the cassette 112 is positioned within the cassette compartment 114 of the PD machine 102 with the door 108 closed, pressure sensors 151A, 151B align with the pressure sensor chambers 163A, 163B. Portions of a membrane that overlies the pressure sensor chambers 163A, 163B adhere to the pressure sensors 151A, 151B using vacuum pressure. Specifically, clearance around the pressure sensors 151A, 151B communicates vacuum to the portions of the cassette membrane overlying the pressure sensing chambers 163A, 163B to hold those portions of the cassette membrane tightly against the pressure sensors 151A, 151B. The pressure of fluid within the pressure sensing chambers 163A, 163B causes the portions of the cassette membrane overlying the pressure sensor chambers 163A, 163B to contact and apply a force to the pressure sensors 151A, 151B.

The pressure sensors 151A, 151B can be any sensors that are capable of measuring the fluid pressure in the pressure sensor chambers 163A, 163B. In some embodiments, the pressure sensors are solid state silicon diaphragm infusion pump force/pressure transducers. One example of such a sensor is the model 1865 force/pressure transducer manufactured by Sensym® Foxboro ICT. In some embodiments, the force/pressure transducer is modified to provide increased voltage output. The force/pressure transducer can, for example, be modified to produce an output signal of 0 to 5 volts.

Figure 3:
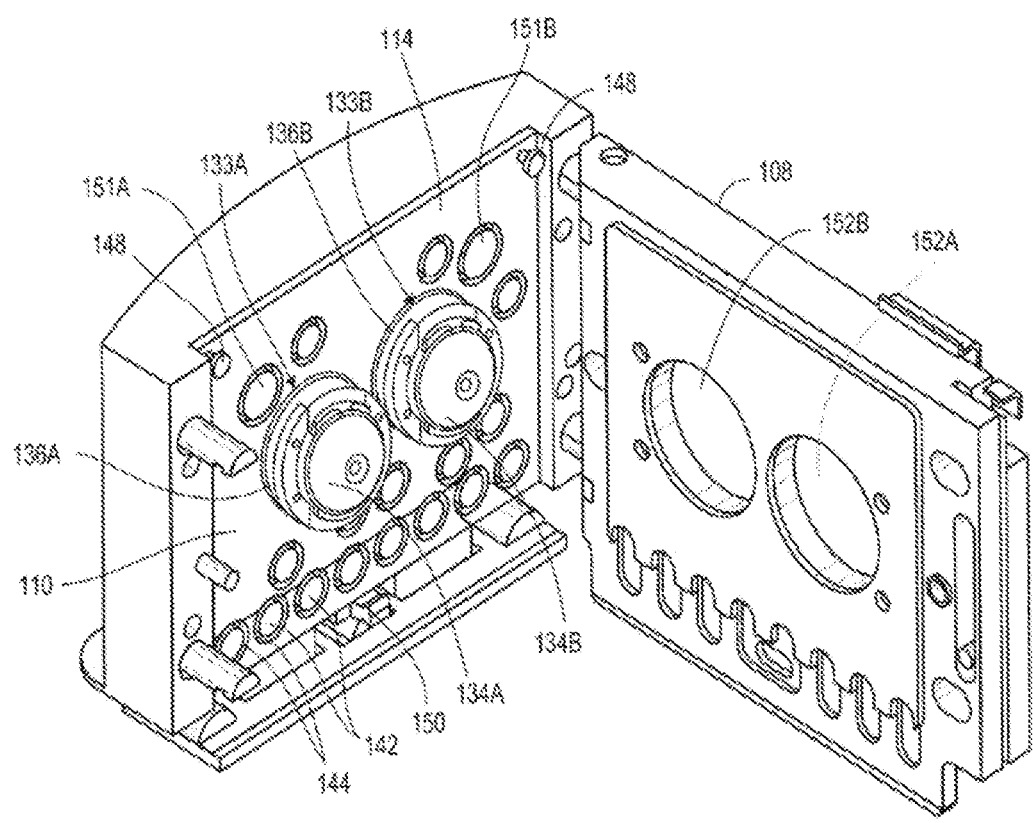
FIG. 3 is a perspective view of an open cassette compartment of the PD machine of FIG. 1, in accordance with some embodiments.

FIG. 3 is a perspective view of an open cassette compartment 114 of the PD machine 102 of FIG. 1, in accordance with some embodiments. As discussed above, the PD machine 102 includes pistons 133A, 133B disposed in piston access ports 136A, 136B, respectively. The PD machine 102 also includes multiple inflatable members 142 positioned within inflatable member ports 144 in the cassette interface 110. The inflatable members 142 align with depressible dome regions of the cassette 112 when the cassette 112 is positioned within the cassette compartment 114 of the PD machine 102. While only a couple of the inflatable members 142 are labeled in FIG. 3, it should be understood that the PD machine 102 includes an inflatable member 142 associated with each of the depressible dome regions of the cassette 112. The inflatable members 142 act, in cooperation with the depressible dome regions, as valves to direct dialysate through the cassette 112 in a desired manner during use. In particular, the inflatable members 142 bulge outward beyond the surface of the cassette interface 110 and into contact with the depressible dome regions of the cassette 112 when inflated, and retract into the inflatable member ports 144 and out of contact with the cassette 112 when deflated. By inflating certain inflatable members 142 to depress their associated dome regions on the cassette 112, certain fluid flow paths within the cassette 112 can be occluded. Thus, dialysate can be pumped through the cassette 112 by actuating the piston heads 134A, 134B, and can be guided along desired flow paths within the cassette 112 by selectively inflating and deflating the various inflatable members 142.

In some embodiments, locating pins 148 extend from the cassette interface 110 of the PD machine 102. When the door 108 is in the open position, the cassette 112 can be loaded onto the cassette interface 110 by positioning the top portion of the cassette 112 under the locating pins 148 and pushing the bottom portion of the cassette 112 toward the cassette interface 110. The cassette 112 is dimensioned to remain securely positioned between the locating pins 148 and a spring loaded latch 150 extending from the cassette interface 110 to allow the door 108 to be closed over the cassette 112. The locating pins 148 help to ensure that proper alignment of the cassette 112 within the cassette compartment 114 is maintained during use.

The door 108 of the PD machine 102 defines cylindrical recesses 152A, 152B that substantially align with the pistons 133A, 133B when the door 108 is in the closed position. When the cassette 112 is positioned within the cassette compartment 114 with the door 108 closed, the pump chambers 138A, 138B at least partially fit within the recesses 152A, 152B. The door 108 further includes a pad that is inflated during use to compress the cassette 112 between the door 108 and the cassette interface 110. With the pad inflated, the portions of the door 108 forming the recesses 152A, 152B support the surface of the pump chambers 138A, 138B, and the other portions of the door 108 support the other regions or surfaces of the cassette 112. The door 108 can counteract the forces applied by the inflatable members 142 and, therefore, allows the inflatable members 142 to actuate the depressible dome regions on the cassette 112. The engagement between the door 108 and the cassette 112 can also help to hold the cassette 112 in a desired position within the cassette compartment 114 to further ensure that the pistons 133A, 133B align with the fluid pump chambers 138A, 138B of the cassette 112.

The control unit 139 of FIG. 1 is connected to the pressure sensors 151A, 151B, to the stepper motors (e.g., the drivers for the stepper motors) that drive the pistons 133A, 133B, and to the encoders that monitor rotation of the lead screws attached to the stepper motors such that the control unit 139 can receive signals from and transmit signals to those components of the PD system 100. The control unit 139 monitors the components to which it is connected to determine whether any complications exist within the PD system 100, such as the presence of an occlusion or blockage in the patient line 130.

Figure 4:
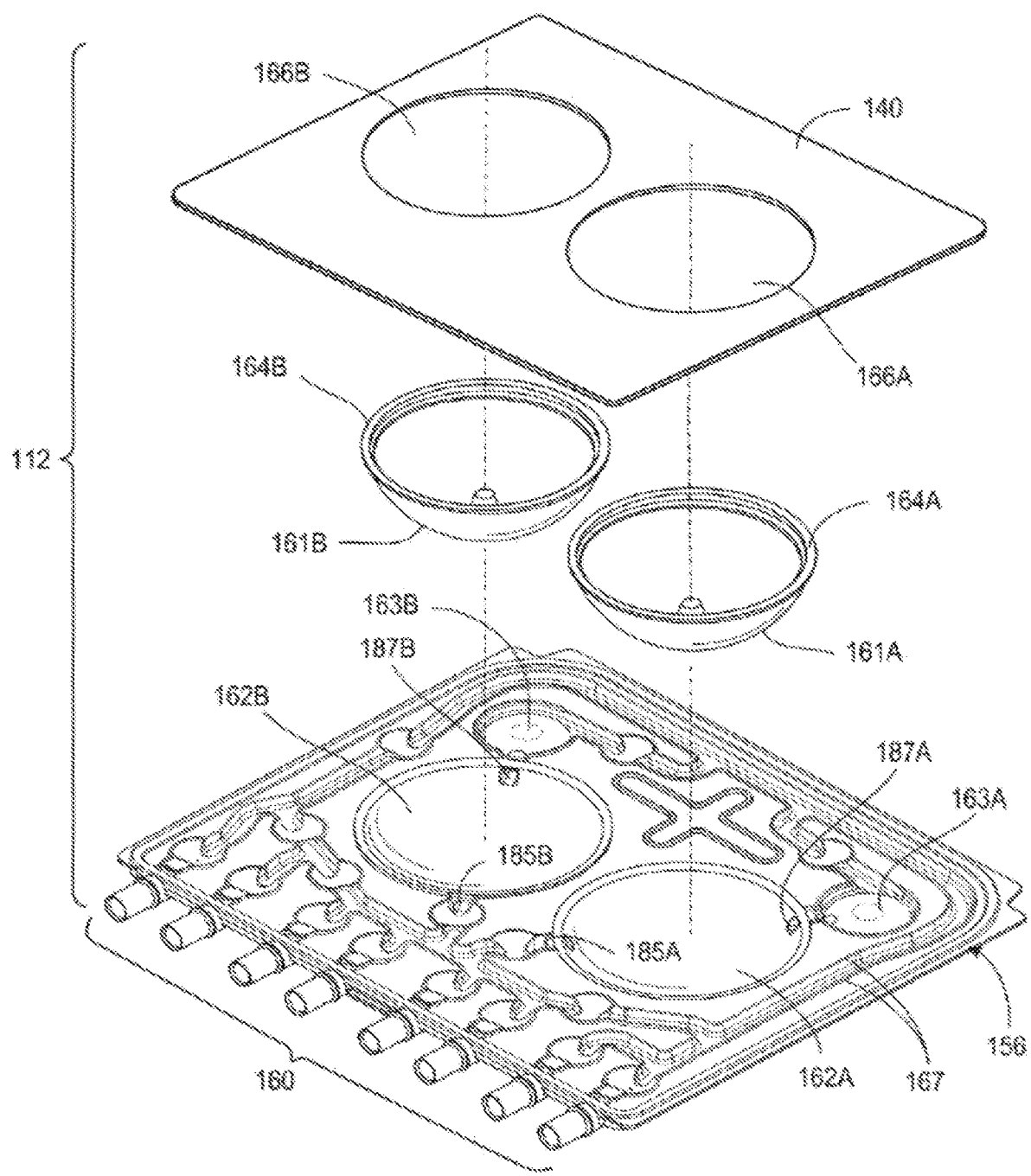
FIG. 4 is an exploded, perspective view of the PD cassette of FIG. 2, in accordance with some embodiments.
Figure 5:
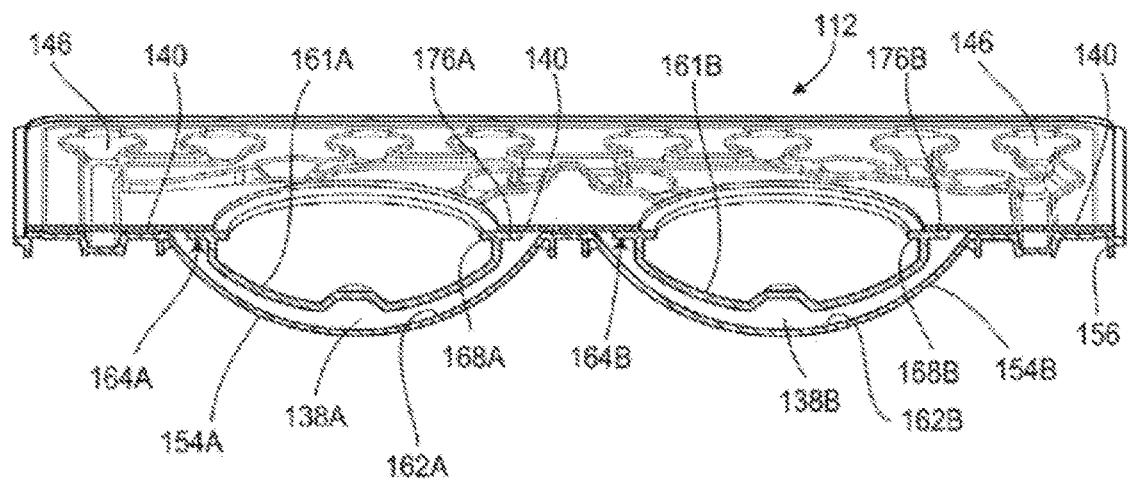
FIG. 5 is a cross-sectional view of the fully assembled PD cassette of FIG. 2, in accordance with some embodiments.
Figure 6:
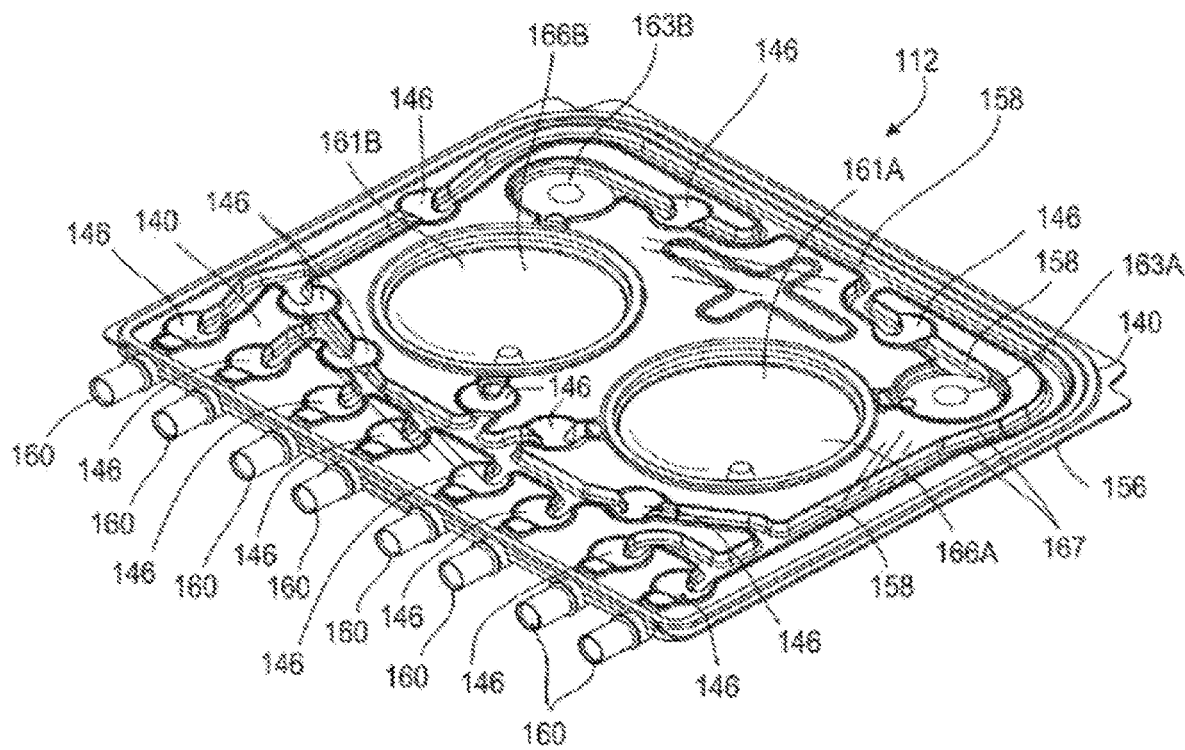
FIGS. 6 and 7 are perspective views of the PD cassette of FIG. 2 from a front side and a back side, respectively, in accordance with some embodiments.
Figure 7:
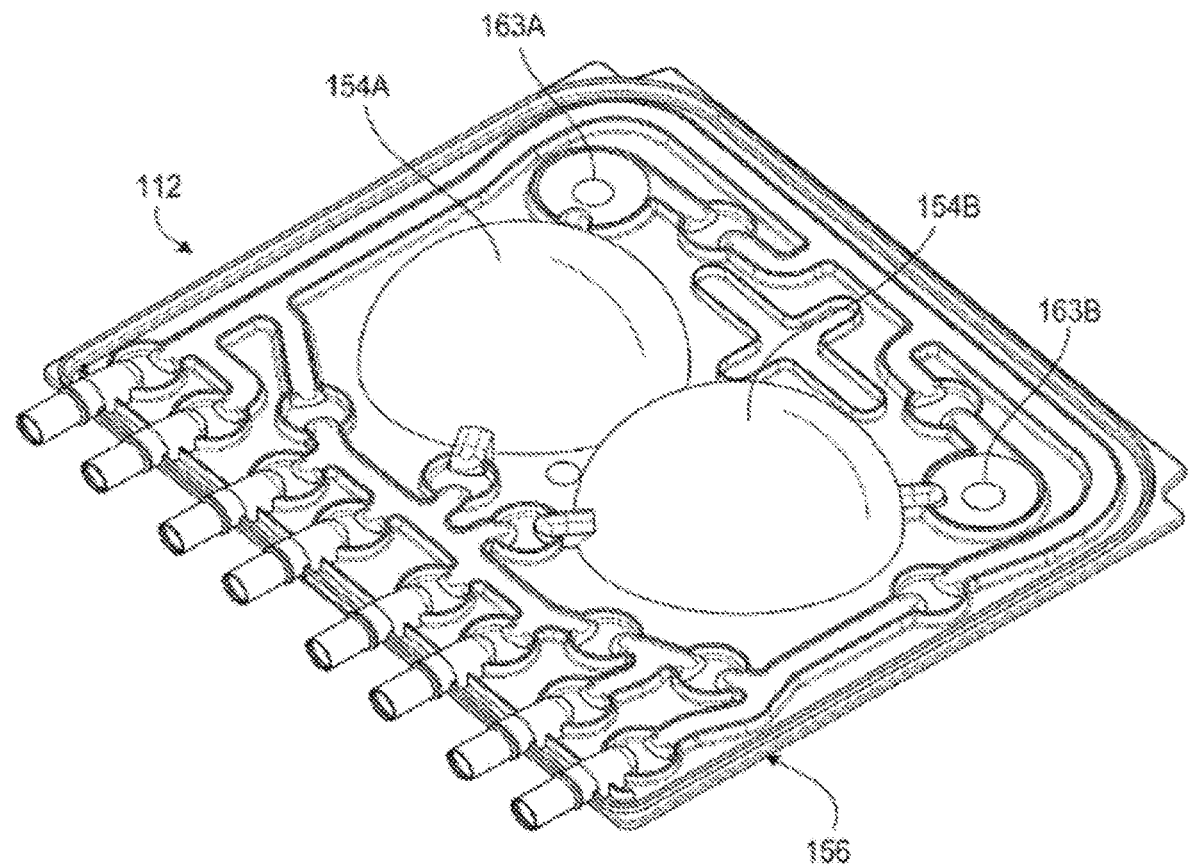

FIG. 4 is an exploded, perspective view of the PD cassette 112 of FIG. 2, in accordance with some embodiments. FIG. 5 is a cross-sectional view of the fully assembled PD cassette 112 of FIG. 2, in accordance with some embodiments. FIGS. 6 and 7 are perspective views of the PD cassette 112 of FIG. 2 from a front side and a back side, respectively, in accordance with some embodiments.

As depicted in FIGS. 4-7, the PD cassette 112 includes a flexible membrane 140 that is attached to a periphery of a tray-like rigid base 156. Rigid dome-shaped fastening members 161A, 161B are positioned within recessed regions 162A, 162B of the base 156. The dome-shaped fastening members 161A, 161B are sized and shaped to receive the piston heads 134A, 134B of the PD machine 102. In some embodiments, the dome-shaped fastening members 161A, 161B have a diameter, measured from the outer edges of annular flanges 164A, 164B, of about 1.5 inches to about 2.5 inches (e.g., about 2.0 inches) and take up about two-thirds to about three-fourths of the area of the recessed regions 162A, 162B. The annular flanges 164A, 164B of the rigid dome-shaped fastening members 161A, 161B are attached in a liquid-tight manner to portions of the inner surface of the membrane 140 surrounding substantially circular apertures 166A, 166B formed in the membrane 140. The annular flanges 164A, 164B of the rigid dome-shaped fastening members 161A, 161B can, for example, be thermally bonded or adhesively bonded to the membrane 140. The apertures 166A, 166B of the membrane 140 expose the rigid dome-shaped fastening members 161A, 161B such that the piston heads 134A, 134B are able to directly contact and mechanically connect to the dome-shaped fastening members 161A, 161B during use.

The annular flanges 164A, 164B of the dome-shaped fastening members 161A, 161B form annular projections 168A, 168B that extend radially inward and annular projections 176A, 176B that extend radially outward from the side walls of the dome-shaped fastening members 161A, 161B. When the piston heads 134A, 134B are mechanically connected to the dome-shaped fastening members 161A, 161B, the radially inward projections 168A, 168B engage the rear angled surfaces of the sliding latches 145A, 147A of the piston heads 134A, 134B to firmly secure the dome-shaped fastening members 161A, 161B to the piston heads 134A, 1334B. Because the membrane 140 is attached to the dome-shaped fastening members 161A, 161B, movement of the dome-shaped fastening members 161A, 161B into and out of the base 156 (e.g., due to reciprocating motion of the pistons 133A, 133B) causes the flexible membrane 140 to similarly be moved into and out of the recessed regions 162A, 162B of the base 156. This movement allows fluid to be forced out of and drawn into the fluid pump chambers 138A, 138B, which are formed between the recessed regions 162A, 162B of the base 156 and the portions of the dome-shaped fastening members 161A, 161B and membrane 140 that overlie those recessed regions 162A, 162B.

Raised ridges 167 extend from the substantially planar surface of the base 156 towards and into contact with the inner surface of the flexible membrane 140 when the cassette 112 is compressed between the door 108 and the cassette interface 110 of the PD machine 102 to form a series of fluid passageways 158 and to form the multiple, depressible dome regions 146, which are widened portions (e.g., substantially circular widened portions) of the fluid pathways 158, as shown in FIG. 6. The fluid passageways 158 fluidly connect the fluid line connectors 160 of the cassette 112, which act as inlet/outlet ports of the cassette 112, to the fluid pump chambers 138A, 138B. As noted above, the various inflatable members 142 of the PD machine 102 act on the cassette 112 during use. The dialysate flows to and from the pump chambers 138A, 138B through the fluid pathways 158 and dome regions 146. At each depressible dome region 146, the membrane 140 can be deflected to contact the planar surface of the base 156 from which the raised ridges 167 extend. Such contact can substantially impede (e.g., prevent) the flow of dialysate along the region of the pathway 158 associated with that dome region 146. Thus, the flow of the dialysate through the cassette 112 can be controlled through the selective depression of the depressible dome regions 146 by selectively inflating the inflatable members 142 of the PD machine 102.

The fluid line connectors 160 are positioned along the bottom edge of the cassette 112. As noted above, the fluid pathways 158 in the cassette 112 lead from the pumping chambers 138A, 138B to the various connectors 160. The connectors 160 are positioned asymmetrically along the width of the cassette 112. The asymmetrical positioning of the connectors 160 helps to ensure that the cassette 112 will be properly positioned in the cassette compartment 114 with the membrane 140 of the cassette 112 facing the cassette interface 110. The connectors 160 are configured to receive fittings on the ends of the dialysate bag lines 126, the heater bag line 128, the patient line 130, and the drain line 132. One end of the fitting can be inserted into and bonded to its respective line and the other end can be inserted into and bonded to its associated connector 160. By permitting the dialysate bag lines 126, the heater bag line 128, the patient line 130, and the drain line 132 to be connected to the cassette 112, as depicted in FIGS. 1 & 2, the connectors 160 allow dialysate to flow into and out of the cassette 112 during use. As the pistons 133A, 133B are reciprocated, the inflatable members 142 can be selectively inflated to allow fluid to flow from any of the lines 126, 128, 130, and 132 to any of ports 185A, 185B, 187A, and 187B of the pump chambers 138A, 138B or to allow fluid to flow from any of ports 185A, 185B, 187A, and 187B of the pump chambers 138A, 138B to any of the lines 126, 128, 130, and 132.

The rigidity of the base 156 helps to hold the cassette 112 in place within the cassette compartment 114 of the PD machine 102 and to prevent the base 156 from flexing and deforming in response to forces applied to the projections 154A, 154B by the dome-shaped fastening members 161A, 161B and in response to forces applied to the planar surface of the base 156 by the inflatable members 142. The dome-shaped fastening members 161A, 161B are also sufficiently rigid that they do not deform as a result of usual pressures that occur in the pump chambers 138A, 138B during the fluid pumping process. Thus, the deformation or bulging of the annular portions 149A, 149B of the membrane 140 can be assumed to be the only factor other than the movement of the pistons 133A, 133B that affects the volume of the pump chambers 138A, 138B during the pumping process.

The base 156 and the dome-shaped fastening members 161A, 161B of the cassette 112 can be formed of any of various relatively rigid materials. In some embodiments, these components of the cassette 112 are formed of one or more polymers, such as polypropylene, polyvinyl chloride, polycarbonate, polysulfone, and other medical grade plastic materials. In some embodiments, these components can be formed of one or more metals or alloys, such as stainless steel. These components can alternatively be formed of various different combinations of the above-noted polymers and/or metals/alloys. These components of the cassette 112 can be formed using any of various different techniques, including machining, molding, and casting techniques.

As noted above, the membrane 140 is attached to the periphery of the base 156 and to the annular flanges 164A, 164B of the dome-shaped fastening members 161A, 161B. The portions of the membrane 140 overlying the remaining portions of the base 156 are typically not attached to the base 156. Rather, these portions of the membrane 140 sit loosely atop the raised ridges 165A, 165B, and 167 extending from the planar surface of the base 156. Any of various attachment techniques, such as adhesive bonding and thermal bonding, can be used to attach the membrane 140 to the periphery of the base 156 and to the dome-shaped fastening members 161A, 161B. The thickness and material(s) of the membrane 140 are selected so that the membrane 140 has sufficient flexibility to flex toward the base 156 in response to the force applied to the membrane 140 by the inflatable members 142. In some embodiments, the membrane 140 is about 0.100 micron to about 0.150 micron in thickness. However, various other thicknesses may be sufficient depending on the type of material used to form the membrane 140. Any of various different materials that permit the membrane 140 to deflect in response to movement of the inflatable members 142 without tearing can be used to form the membrane 140. In some embodiments, the membrane 140 includes a three-layer laminate. In some embodiments, inner and outer layers of the laminate are formed of a compound that is made up of 60 percent Septon® 8004 thermoplastic rubber (i.e., hydrogenated styenic block copolymer) and 40 percent ethylene, and a middle layer is formed of a compound that is made up of 25 percent Tuftec® H1062 (SEBS: hydrogenated styrenic thermoplastic elastomer), 40 percent Engage® 8003 polyolefin elastomer (ethylene octane copolymer), and 35 percent Septon® 8004 thermoplastic rubber (i.e., hydrogenated styenic block copolymer). The membrane 140 can alternatively include more or fewer layers and/or can be formed of different materials.

Figure 8:
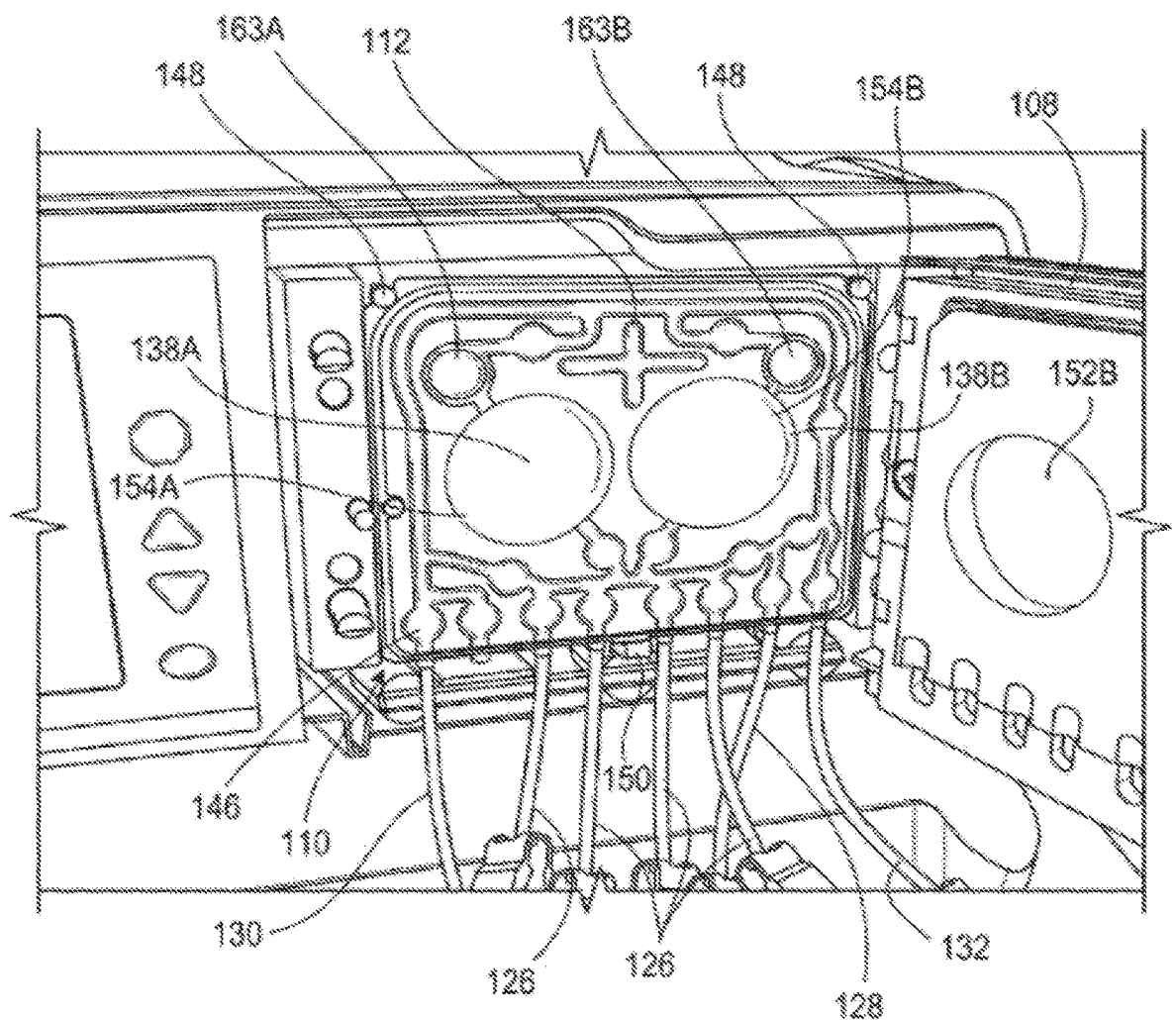
FIG. 8 illustrates the PD cassette seated against the cassette interface, in accordance with some embodiments.

FIG. 8 illustrates the PD cassette 112 seated against the cassette interface 110, in accordance with some embodiments. As depicted in FIG. 8, before starting a PD treatment, the door 108 of the PD machine 102 is opened to expose the cassette interface 110, and the cassette 112 is positioned with the dome-shaped fastening members 161A, 161B aligned with the pistons 133A, 133B of the PD machine 102, the pressure sensing chambers 163A, 163B aligned with the pressure sensors 151A, 151B of the PD machine 102, the depressible dome regions 146 aligned with the inflatable members 142 of the PD machine 102, and the membrane 140 adjacent to the cassette interface 110. In order to ensure that the cassette 112 is properly positioned on the cassette interface 110, the cassette 112 is positioned between the locating pins 148 and the spring loaded latch 150 extending from the cassette interface 110. The asymmetrically positioned connectors 160 of the cassette 112 act as a keying feature that reduces the likelihood that the cassette 112 will be installed with the membrane 140 and dome-shaped fastening members 161A, 161B facing in the wrong direction (e.g., facing outward toward the door 108). Additionally or alternatively, the locating pins 148 can be dimensioned to be less than the maximum protrusion of the projections 154A, 154B such that the cassette 112 cannot contact the locating pins 148 if the membrane 140 is facing outward towards the door 108. The pistons 133A, 133B are typically retracted into the piston access ports 136A, 136B during installation of the cassette 112 to avoid interference between pistons 133A, 133B and the dome-shaped fastening members 161A, 161B and, therefore, increase the ease with which the cassette 112 can be positioned within the cassette compartment 114.

After positioning the cassette 112 as desired on the cassette interface 110, the door 108 is closed and the inflatable pad within the door 108 is inflated to compress the cassette 112 between the inflatable pad and the cassette interface 110. The compression of the cassette 112 holds the projections 154A, 154B of the cassette 112 in the recesses 152A, 152B of the door 108 and presses the membrane 140 tightly against the raised ridges 167 extending from the planar surface of the rigid base 156 to form the enclosed fluid pathways 158 and dome regions 146. The patient line 130 is then connected to a patient's abdomen via a catheter, and the drain line 132 is connected to a drain or drain receptacle. In addition, the heater bag line 128 is connected to the heater bag 124, and the dialysate bag lines 126 are connected to the dialysate bags 122. At this point, the pistons 133A, 133B can be coupled to the dome-shaped fastening members 161A, 161B of the cassette 112 to permit priming of the cassette 112 and one or more of the lines 126, 128, 130, and 132. Once these components have been primed, the PD treatment can be initiated.

Integrated Safety Mechanism

Figure 9:
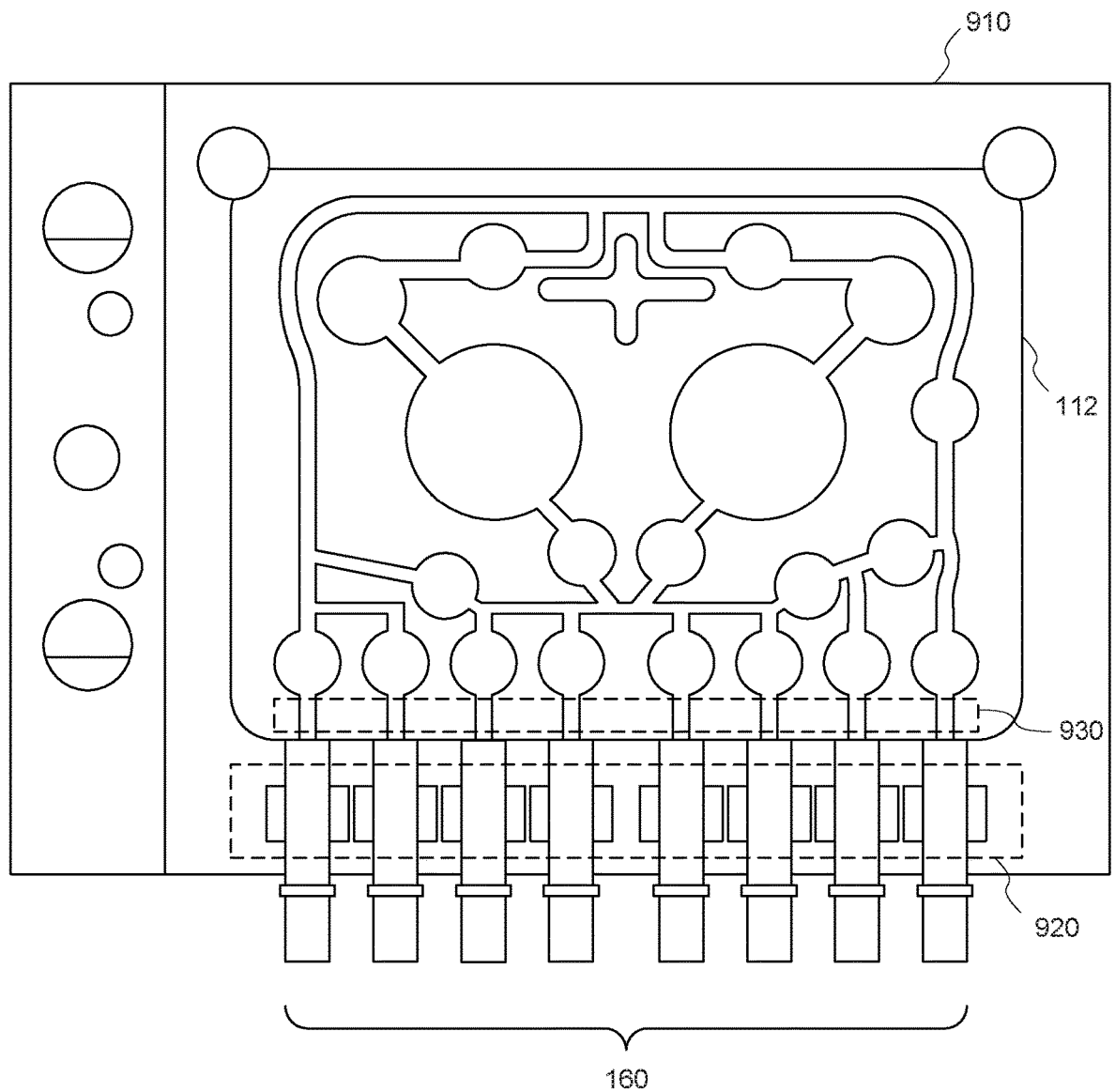
FIG. 9. illustrates a modified cassette interface of the PD machine, in accordance with some embodiments.

FIG. 9 illustrates a modified cassette interface 910 of the PD machine 102, in accordance with some embodiments.

The modified cassette interface 910 is similar to cassette interface 110, described above, except that additional openings 920 are machined into the interface to enable a safety mechanism to be implemented by the PD machine 102. In an embodiment, each fluid line connector 160 attached to a port of the cassette 112 extends past one of the openings 920. The safety mechanism can be activated to pinch (e.g., compress) a distensible tube connected between the fluid line connector 160 and a fluid pathway in the cassette 112, thereby preventing the flow of fluid through the distensible tube. In the event of an error detected by the PD machine 102 during a PD treatment cycle, the PD machine 102 can activate one or more safety mechanisms to quickly shut off the flow of fluid to/from one or more fluid lines connected to the fluid line connectors 160. In this manner, the safety mechanisms can prevent potential contamination of the patient and/or prevent backflow of effluent into the clean dialysate bags.

It will be appreciated that, when compared to illustrations of the cassette 112 and the fluid connectors 160, such as shown in FIG. 6, the fluid connectors 160 can be coupled to a distensible tube between the fluid line connector 160 and the cassette 112. In some embodiments, the fluid line connectors are made of a hard plastic material or other type of material that is not easily deformed. Rather than bonding the hard plastic connector directly to the cassette 112, the disposable cassette 112 assembly can be modified to add distensible tubing disposed between the cassette 112 and the fluid line connectors 160. The short sections of distensible tubing can be easily compressed by the safety mechanism in order to cut off the fluid pathway within the tubing.

In other embodiments, the distensible tubing is omitted and the openings 920 are placed in a different area of the cassette interface 110 that overlaps the cassette 112 such that the safety mechanism engages with and/or compresses the channels or fluid pathways formed in the cassette 112. For example, the openings 920 could be moved to overlap with the region 930 such that the safety mechanism is activated to compress the corresponding channel in the cassette 112 that connects the fluid line connector 160 to the dome regions 146. It will be appreciated that the channels in the cassette 112 might be easier to compress than the distensible tube and, as a result, the safety mechanism may require less force to shut off the fluid flow from the fluid lines connected to the cassette 112.

Figure 10:
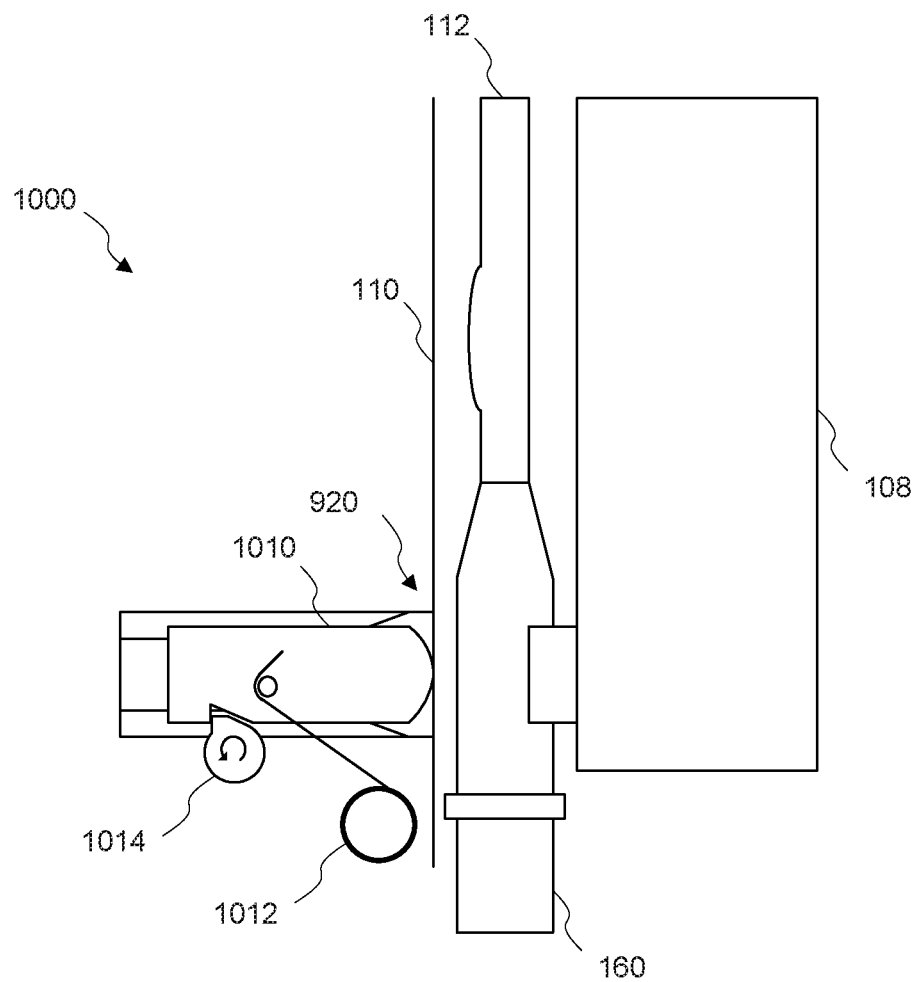
FIG. 10 illustrates the safety mechanism, in accordance with some embodiments.

FIG. 10 illustrates the safety mechanism 1000, in accordance with some embodiments. The safety mechanism 1000 is illustrated in a side view with the cassette 112 disposed between the cassette interface 110 and the door 108, which is closed. In some embodiments, the door 108 may be modified such that a surface of the door 108 proximate the distensible tubes opposite the openings 920 in the cassette interface 110 extends towards the distensible tubes to restrict movement of the distensible tubes relative to the safety mechanism. In some cases, the door 108 includes a structural member that, when closed, forces the distensible tubes against a surface of the cassette interface 110 proximate the openings 920. A distance between the surface of the cassette interface 110 and the structural member is sufficient that a fluid path within the tube is capable of allowing fluid to pass when the safety mechanism 100 is not engaged (e.g., when the safety mechanism is retracted into the opening 920).

In an embodiment, the safety mechanism 1000 includes a compression member 1010 that is spring-loaded to extend from the opening 920 in the cassette interface 110. A spring 1012 can be attached to the compression member 1010 and configured to apply a force to the compression member 1010 to bias the compression member 1010 into an extended position. As used herein, the extended position refers to a state where at least a portion of the compression member 1010 extends past a plane of the cassette interface 110 and contacts (and depresses) the distensible tube connected to the cassette 112 and/or the fluid line connector 160. In an embodiment, the force of the spring 1012 and the length and/or travel of the compression member 1010 are sufficient to enable the compression member to fully compress the distensible tube to prevent any fluid from flowing from the cassette 112 to the fluid line connector 160 or from the fluid line connector 160 to the cassette 112.

In an embodiment, the compression member 1010 is retained in the retracted position by a sear component 1014. The sear component 1014 is a cam that interacts with a feature formed in the compression member 1010. When the sear component 1014 rotates to a first position, a flat surface on the cam locks in the feature and prevents the compression member 1010 from extending out of the opening 920. By rotating the cam, the flat surface will slide against the corresponding surface of the feature in the compression member 1010 until the interference no longer exists, allowing the spring 1012 to drive the compression member 1010 out of the opening 920 in accordance with the spring force.

Figure 11:
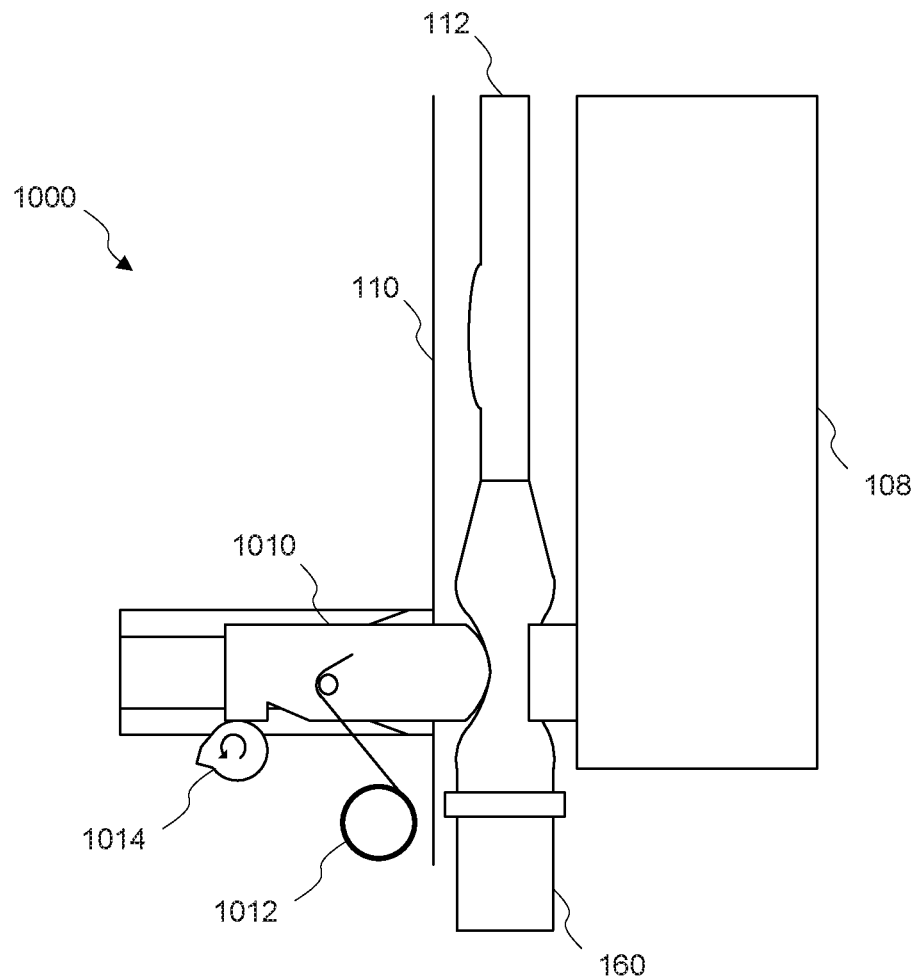
FIG. 11 illustrates the safety mechanism in an activated state, in accordance with some embodiments.

FIG. 11 illustrates the safety mechanism 1000 in an activated state, in accordance with some embodiments. As shown in FIG. 11, the sear component 1014 has rotated counter clockwise, thereby releasing the compression member 1010 to allow the compression member to spring forward and extend from the opening 920, thereby compressing the distensible tube between the cassette 112 and the fluid line connector 160.

Once the safety mechanism 1000 is activated, the compression member 1010 must be manually pushed back into the opening 920 such that the feature in the compression member 1010 can be engaged by the sear component 1014 in order to restrain the compression member 1010 in the retracted state. As used herein, the retracted state can correspond to the safety mechanism 1000 being disengaged or deactivated, whereas the extended state can correspond to the safety mechanism 1000 being engage or activated.

In an embodiment, the sear component 1014 can be coupled to a motor (e.g., electrical motor, stepper motor, etc.) that drives the rotation of the cam to engage the feature of the compression member 1010 and/or release the compression member 1010. In some embodiments, the cam can include multiple flat surfaces that are configured to rotate and automatically engage the feature in the compression member 1010 when the compression member 1010 is forced back into the opening 920.

In an embodiment, the PD machine 102 includes a plurality of safety mechanisms 1000, each corresponding to a different fluid line coupled to the cassette 112. Each safety mechanism can be actuated by a separate actuator to shut off the fluid pathway to a corresponding fluid line, while other lines remain open. In another embodiment, the sear components 1014 for multiple safety mechanisms are driven by a single actuator such that two or more lines will be shut off simultaneously due to the operation of the sear component 1014 in multiple safety mechanisms 1000. For example, the cams of the sear components 1014 can be coupled to a single shaft that is driven by a stepper motor or other type of actuator. Rotating the shaft will rotate all of the cams simultaneously, releasing multiple compression members 1010 at once.

It will be appreciated that the safety mechanism 1000 is only one exemplary embodiment of the components designed to compress the distensible tube in order to cut off fluid flow between a corresponding fluid line and the cassette 112. Modifications to the components shown in FIGS. 10-11 are contemplated and within the scope of the present disclosure. For example, the spring 1012 shown in FIGS. 10-11 is a torsion spring that attaches to a protrusion or other type of feature on the compression member 1010 in order to impart a force on the compression member. In other embodiments, the spring 1012 can be implemented as a compression spring, Belleville spring stack, and/or an extension spring. In other embodiments, the spring 1012 can be omitted and replaced with another mechanism for driving the compression member 1010 to extend from the opening 920 and contact the distensible tube. For example, the compression member 1010 could be connected to an electric or pneumatic actuator that is configured to impart a force on the compression member 1010 to extend the compression member out of the opening 920.

In some embodiments, the safety mechanism 1000 also includes a separate actuator for retracting the compression member 1010 into the opening 920 such that the safety mechanism 1000 can be disengaged automatically. For example, a pneumatic solenoid valve can be activated to force air into a pneumatic cylinder that forces the compression member 1010 to retract into the opening 920. The pneumatic cylinder is powerful enough to overcome the spring force when activated, and can be deactivated (i.e., air is not forced into the cylinder) to allow the spring 1012 to drive the compression member 1010 out of the opening when the safety mechanism 1000 is activated.

Figure 12:
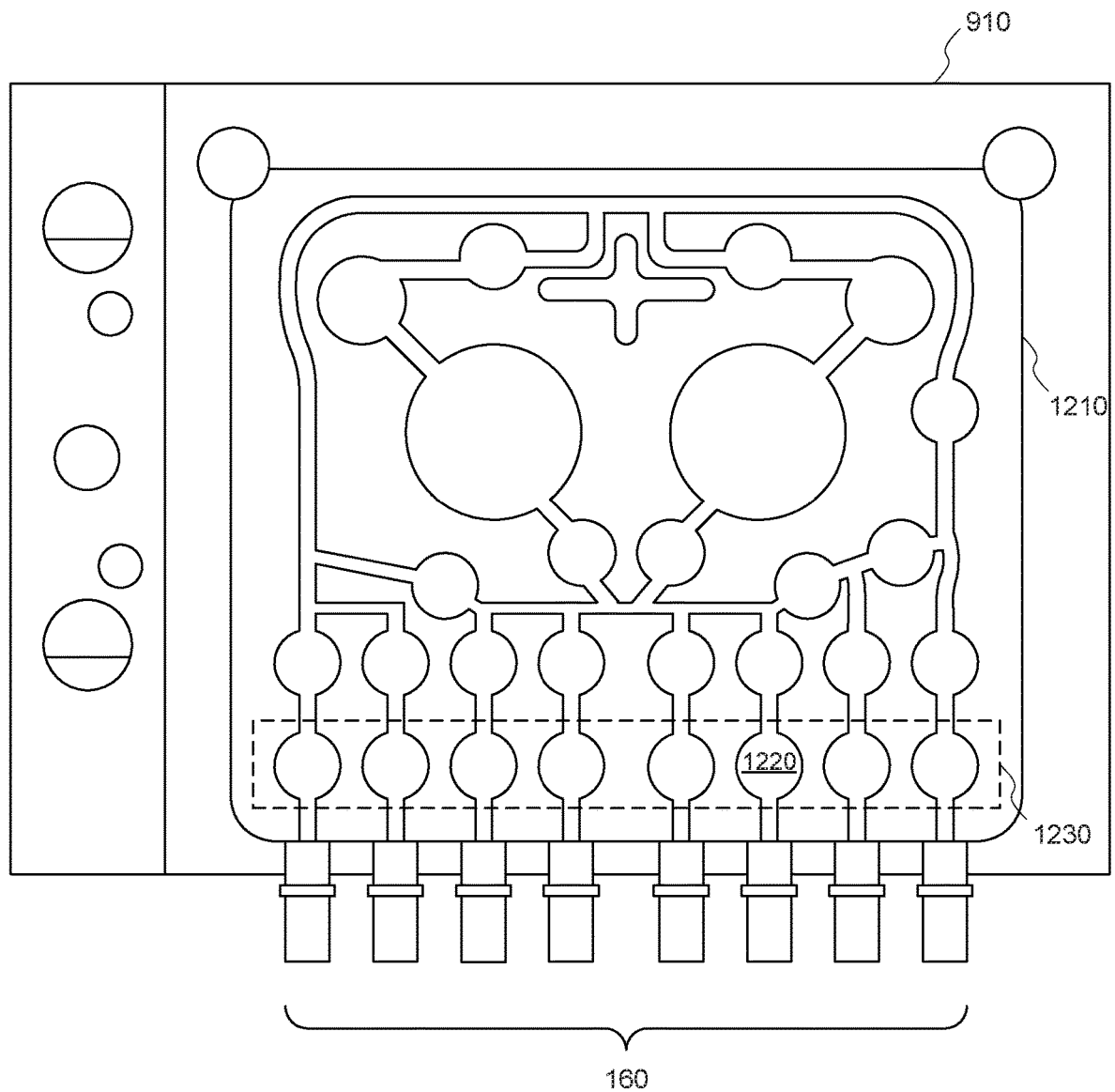
FIG. 12 illustrates a modified cassette configured to be used with an integrated safety mechanism of a PD machine, in accordance with some embodiments.

FIG. 12 illustrates a modified cassette 1210 configured to be used with an integrated safety mechanism of a PD machine 102, in accordance with some embodiments. The safety mechanism 1000 shown above is designed to cut off fluid lines by compressing the distensible tube that connects a fluid connector 160 to the cassette 112. However, in other embodiments, the cassette 112 can be modified to include additional dome regions 1220 integrated into the cassette 1210 in order to perform a similar function.

In an embodiment, the cassette 1210 is extended in a vertical dimension to allow for a second row 1230 of dome regions 1220 to be formed between the row of dome regions 146, as described above, and the fluid connectors 160. The dome regions 1220 can be aligned with the safety mechanisms 1000 such that the dome is compressed when the safety mechanism 1000 is activated.

In other embodiments, the safety mechanisms are implemented as a plurality of inflatable members installed in additional inflatable member ports, similar to the inflatable members 142 and inflatable member ports 144, described above. In such embodiments, the safety mechanisms can be activated with compressed air and one or more valves, rather than spring activated as shown in safety mechanism 1000.

Figure 13:
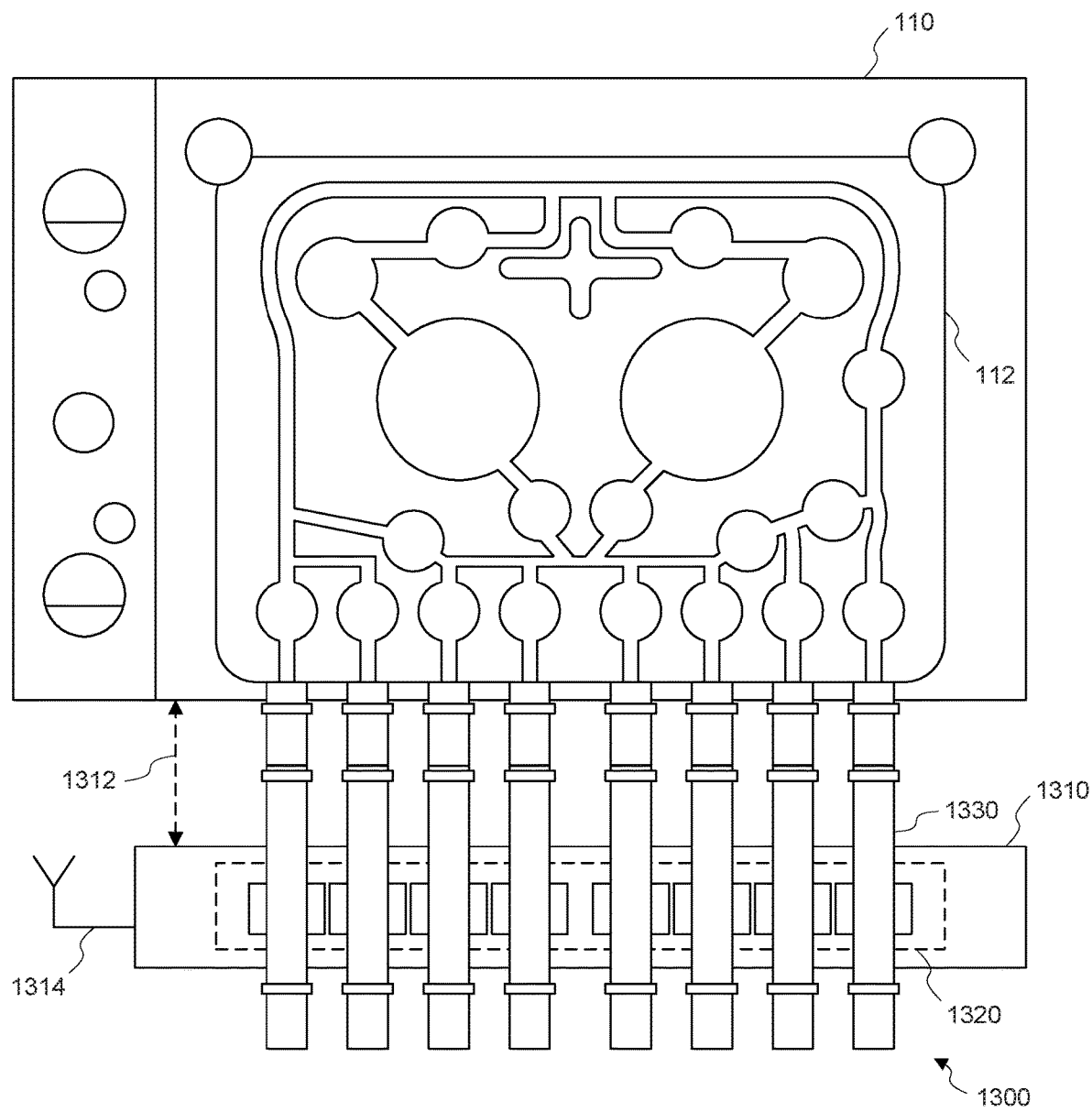
FIG. 13 illustrates a safety module for use with a legacy PD machine, in accordance with some embodiments.

FIG. 13 illustrates a safety module 1300 for use with a legacy PD machine 102, in accordance with some embodiments. The safety mechanism 1000, described above, is built in to newer PD machines 102 that have modified either the cassette interface 110, the door 108, the cassette 112, or any combination of the aforementioned components of the PD machine 102. In some cases, it can be desired to retrofit existing PD machines 102 to incorporate a new function such as the safety mechanism 1000.

In some embodiments, the safety module 1300 is provided as a separate component that, e.g., can be placed under the existing PD machine 102 and interfaces with the cassette 112. The safety module 1300 can include a chassis and a door (not explicitly shown). The door can open to reveal an interface 1310 that includes a number of openings 1320 corresponding to a plurality of safety mechanisms 1000. Extension lines 1330, comprising distensible tubes with fluid line connectors attached thereto, are connected to the fluid line connectors 160 of the cassette and drop down in front of the openings 1320. The door of the safety module 1300 can be closed over the extension lines 1330, and the safety mechanisms 1000 operate to shut off fluid flow through the extension lines. In some embodiments, the cassette 112 can be modified to include distensible tubes disposed between the cassette 112 and the fluid connectors 160 that are long enough to be used with the safety module 1300 without the addition of the extension lines 1330.

In an embodiment, the safety module 1300 includes a processor, a memory, and a communications interface for communicating with the PD machine 102 such that the PD machine 102 can be installed with software that allows the PD machine 102 to send signals to the safety module 1300 for operating (e.g., activating/deactivating) the safety mechanisms 1000. In an embodiment, the communications interface is a wired interface 1312 that can be connected to a communications port (e.g., a serial port, a USB port, etc.) for facilitating communication between the PD machine 102 and the safety module 1300. In another embodiment, the communications interface is a wireless interface 1314 that utilizes a transceiver and one or more antennas to communicate with the PD machine 102 through, e.g., Wi-Fi, Bluetooth, or some other near field communication protocol.

Figure 14:
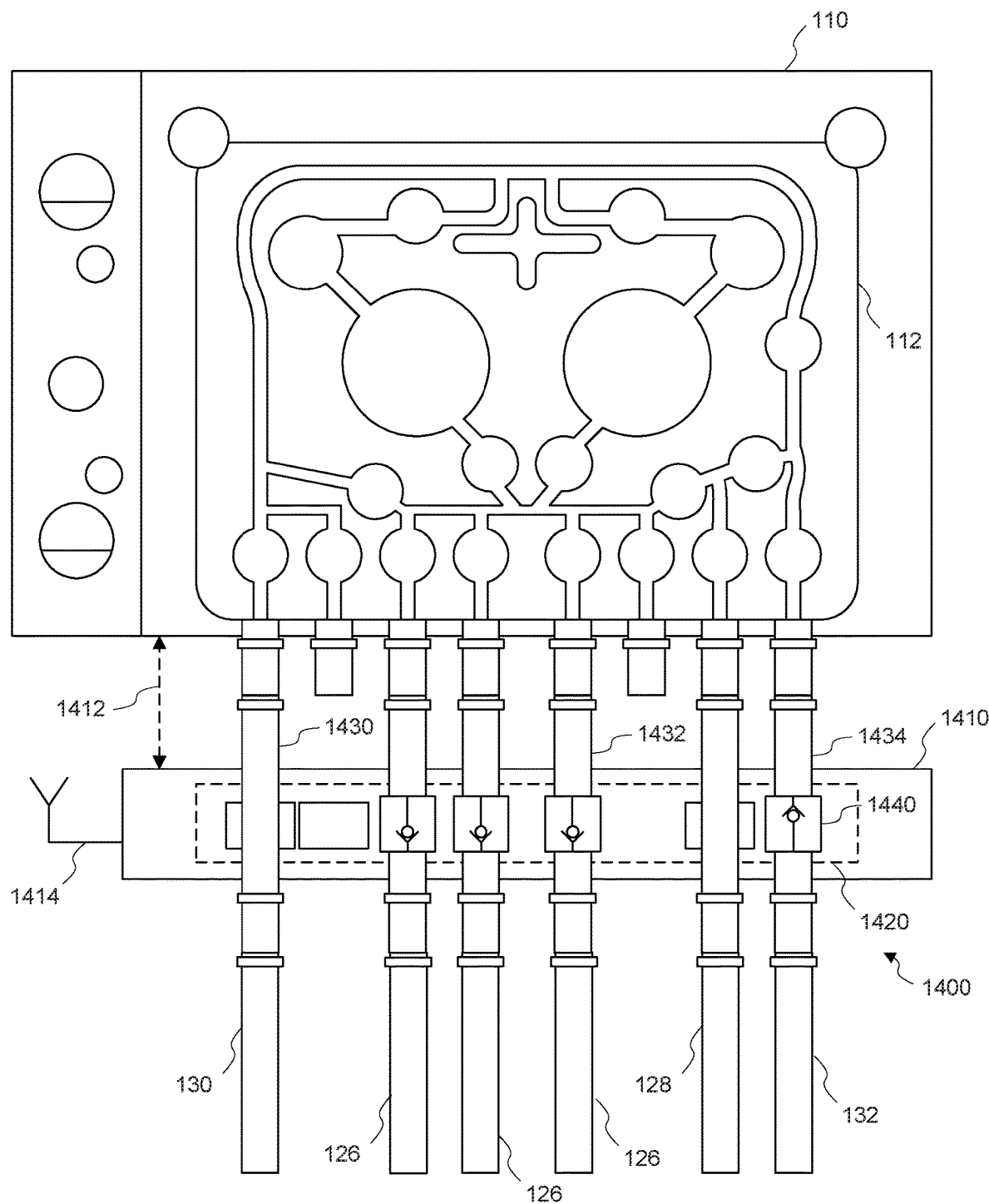
FIG. 14 illustrates a safety module, in accordance with some embodiments.

FIG. 14 illustrates a safety module 1400, in accordance with some embodiments. Although safety mechanism 1000 utilizes a clamping pressure to close a distensible tube, other types or varieties of safety mechanism are contemplated as being within the scope of the present disclosure. In some embodiments, at least some of the safety mechanisms 1000 can be replaced with a one-way check valve. For example, fluid flow to the drain line 132 or from the dialysate bags 126 can utilize check valves as a safety mechanism to ensure that fluid flow direction is always in one direction (e.g., from the sterile dialysate bags or to the drain line). The use of check valves 1440 to prevent backflow could be sufficient to replace at least a portion of the safety mechanisms 1000 in the safety module 1400 and can reduce the cost and/or complexity of the safety module 1400.

As shown in FIG. 14, the safety module 1400 is similar to the safety module 1300 except the number of opening 1420 and the number of safety mechanisms 1000 disposed in those openings 1420 is reduced. Similar to the safety module 1300, the safety module 1400 includes an interface 1410 and a door (not explicitly shown). The safety module 1400 also includes a wired 1412 or wireless 1414 communications interface. Extension lines 1430 are connected to the fluid line connectors 160 of the cassette 112 and, at the other end, connected to the patient line 130 and the heater bag line 128. Additional extension lines 1432 are connected to the fluid line connectors 160 of the cassette 112 and, at the other end, connected to the dialysate bag line(s) 126. The extension lines 1432 include a one-way check valve 1440 that allows fluid flow in one direction from the dialysate bag line 126 to the cassette 112. An additional extension line 1434 is connected to the fluid line connector 160 of the cassette 112 and, at the other end, connected to the drain line 132. The extension line 1434 includes a one-way check valve 1440 that allows fluid flow in one direction from the cassette 112 to the drain line 132.

It will be appreciated that the use of check valves 1440 instead of the spring-loaded safety mechanism 1000 can decrease the number of safety mechanisms 1000 in the safety module 1400 from eight to three, which can reduce the cost and/or complexity of the safety module 1400. However, the check valves 1440 cannot be operated by the PD machine 102 and, in the event of a leak in the cassette 112, can still allow fluid to drain from the dialysate bags connected to the dialysate bag lines 126 unrestricted. While the check valves 1440 do not prevent all fluid flow into the cassette 112, the safety mechanisms 1000 will prevent contamination of the patient line 130 and/or the heater bag line 128.

In other embodiments, the safety mechanisms 1000 can be retained for the dialysate bag lines 126 and only the drain line 132 is connected via a check valve 1440. In yet other embodiments, the drain line 132 does not have either a check valve or a safety mechanism 1000 and is simply allowed to drain freely to the drain.

It will also be appreciated that, in some embodiments, a check valve can be included in the extension lines 1430 corresponding to a spring-loaded safety mechanism 1000. In other words, the safety mechanism for some fluid lines, such as the dialysate bag lines 126, can be operated with a check valve in the fluid path as well as by using the clamping feature of a distensible tube located proximate the safety mechanism 1000. Multiple safety features can be incorporated into the fluid path associated with any particular fluid line.

Figure 15:
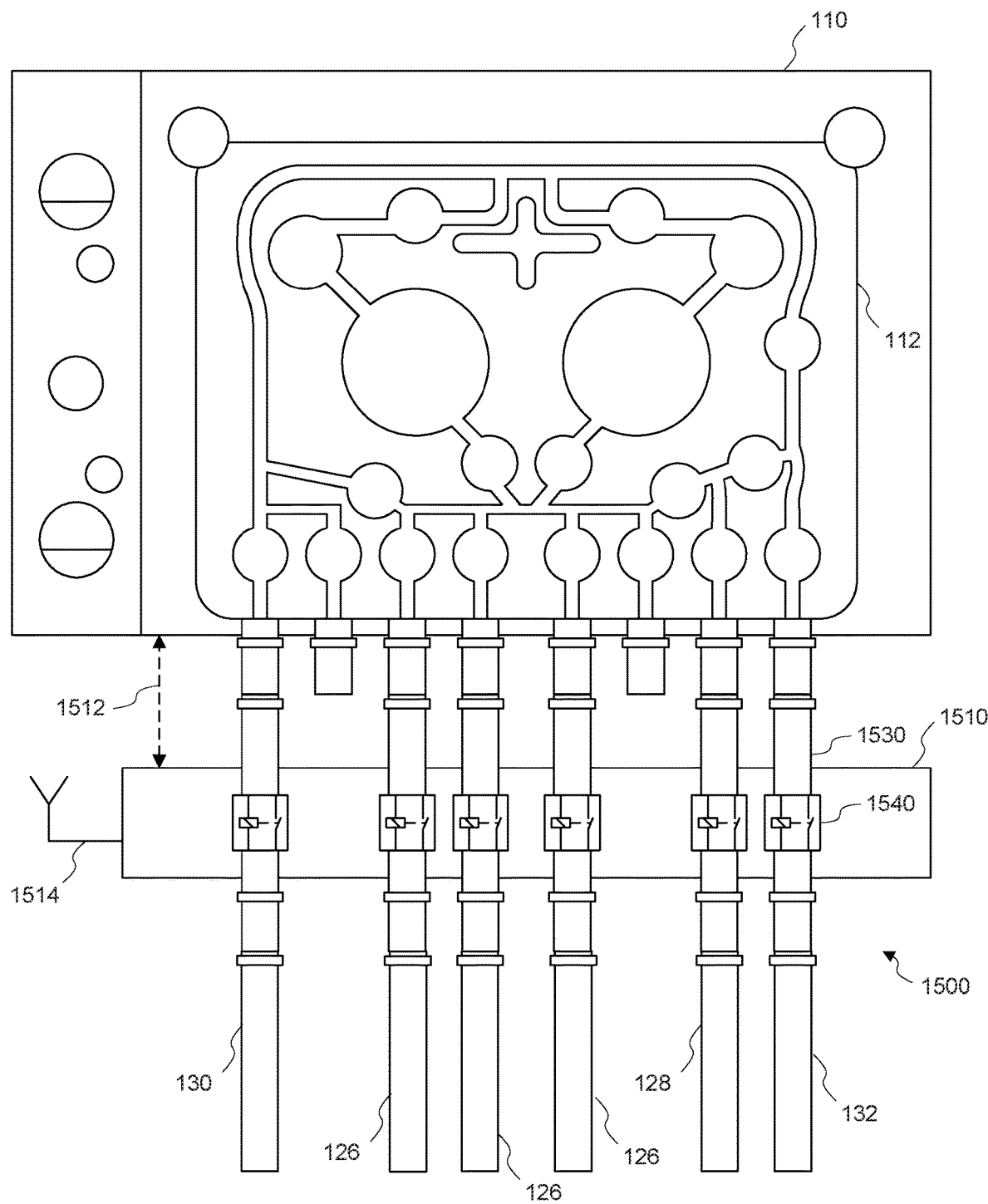
FIG. 15 illustrates a safety module, in accordance with some embodiments.

FIG. 15 illustrates a safety module 1500, in accordance with some embodiments. The safety mechanism 1000, or other spring-loaded varieties that are configured to apply a clamping force to a distensible tube, are not an exclusive means for implementing the safety feature of shutting off flow of the fluid lines connected to the cassette 112. In some embodiments, the safety mechanism 1000 can be replaced by a relay solenoid 1540 that, when power is applied, allows bi-directional fluid flow through the valve portion of the relay solenoid 1540. If power to the relay solenoid 1540 is cutoff, either through intentional activation of the safety mechanism or through power loss to the safety module 1500/PD machine 102, then the relay solenoid 1540 closes the valve and prevents fluid flow through the extension line 1530 disposed between the fluid line connectors 160 of the cassette 112 and the corresponding fluid lines (e.g., patient line 130, dialysate bag lines 126, heater bag line 128, or drain line 132).

It will be appreciated that the safety module 1500 can include an interface 1510 and, optionally, a door, similar to those described above for safety modules 1300/1400. The safety module 1500 also includes either a wired 1512 or a wireless 1514 communications interface. In other embodiments, the interface 1510 is a component of the chassis that is used to secure the relay solenoids 1540 to the safety module 1500.

It will be appreciated that the cassette 112 and fluid lines are disposable because they may come in contact with effluent flushed from the peritoneal cavity. In order to keep the system sterile, the extension lines 1530 should be disposable as well. In an embodiment, the relay solenoids 1540 are split into two components, an electro-magnetic portion (e.g., a relay connected to a solenoid that generates a force on a cylinder) and a valve (e.g., a mechanism that connects to the cylinder in the solenoid to open and close the fluid path in the extension line). The valve portion can include a plastic poppet valve, normally held closed by a spring, that is opened when the solenoid is powered and forces the cylinder to open the poppet valve). By allowing the valve portion to be disconnected from the electro-magnetic portion, costs of the disposable extension lines 1530 can be reduced.

It will be appreciated that the features of the safety modules 1300/1400/1500 described above, in some embodiments, can be incorporated directly into a PD machine 102 rather than implemented as an auxiliary unit.

Figure 16:
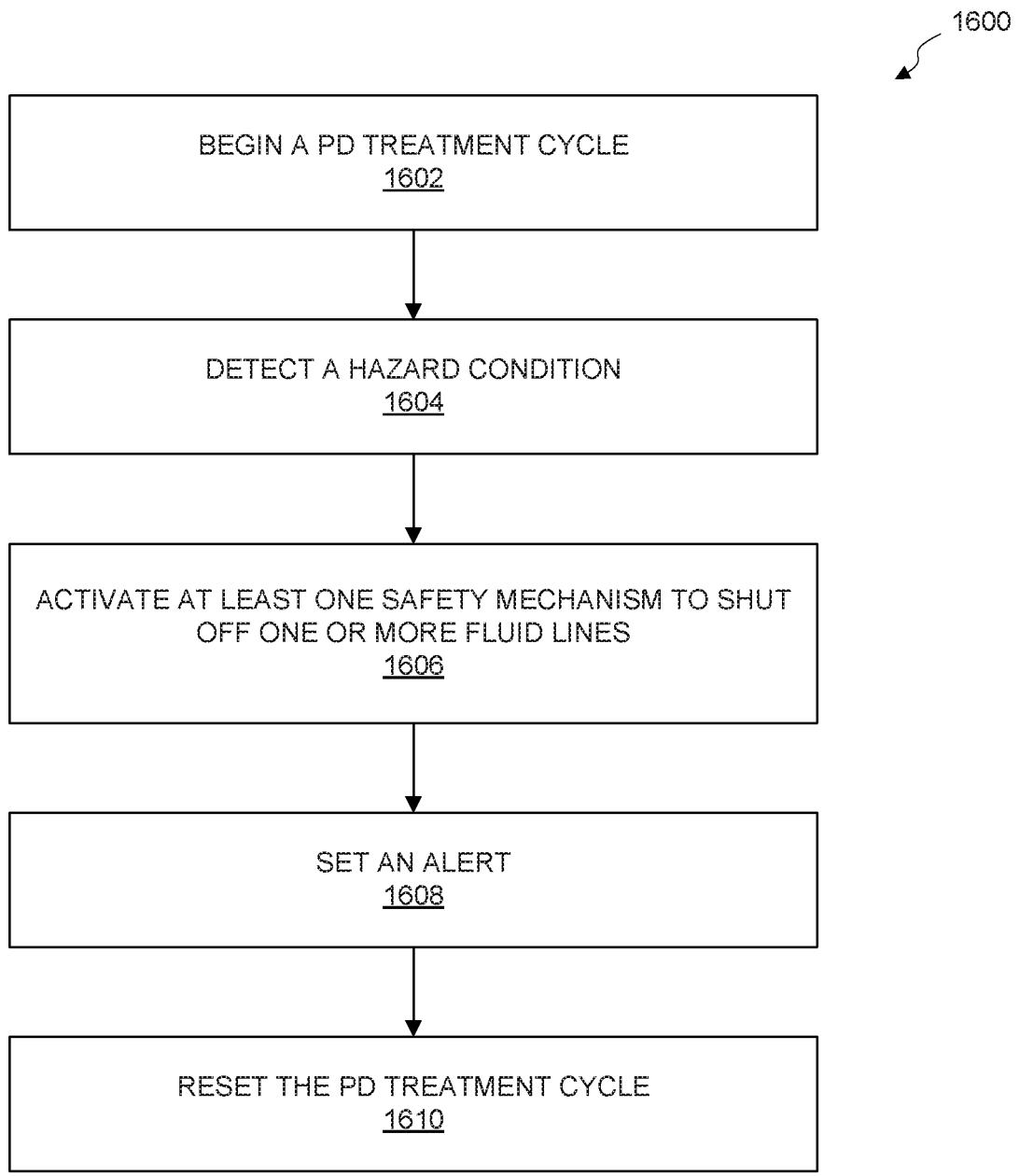
FIG. 16 is a flow diagram of method for operating a PD machine that includes a safety mechanism, in accordance with some embodiments.

FIG. 16 is a flow diagram of method 1600 for operating a PD machine 102 that includes a safety mechanism, in accordance with some embodiments. It will be appreciated that the method 1600 is described as being performed by the PD machine 102 and/or the safety modules 1300/1400/1500. More specifically, the various steps described below can be implemented by a processor, such as the control unit 139 of the PD machine 102, configured to execute a number of instructions. In various embodiments, the method 1600 can be implemented using hardware, software executed by a general purpose processor configured to control a specialized apparatus such as a PD machine, or a combination of hardware and software.

At step 1602, a PD machine 102 begins a PD treatment cycle. In an embodiment, power is applied to the PD machine 102, the patient or caretaker is prompted to insert the cassette 112 and connect one or more fluid lines to the cassette 112, and close the door 108 of the PD machine 102. In some embodiments, the patient or caretaker connects the fluid lines to one or more extension lines of an auxiliary safety module and then connects the extension lines to the fluid line connectors 160 of the cassette 112. Once the connections have been made, the PD machine 102 begins the fill/dwell/drain cycles of the PD treatment.

At step 1604, the PD machine 102 detects a hazard condition. In an embodiment, one or more sensors are used to monitor parameters of the PD treatment. Examples of the sensors include a load cell (to monitor the weight of the heater bag), flow sensors, capacitive sensors (to monitor for leaks), pressure transducers (to monitor fluid volume in the cassette 112), and the like. Detecting the hazard condition can include, but is not limited to, detecting an occlusion in a fluid line, detecting a lack of fluid pressure in the pump chambers 138 of the cassette 112, or detecting fluid detected on a surface of the cassette interface 110. The hazard condition can also include expiration of a timer (e.g., indicating fluid flow to or from the patient line is too slow), loss of power, or user input (e.g., manual indication through a menu item of a user interface or a switch (e.g., e-stop switch)).

In some embodiments, the safety mechanisms can be operated manually through a user interface. For example, control elements (e.g., touch-screen buttons, dome push buttons, etc.) can be used to activate or deactivate each of the safety mechanisms, either individually or as a group or subgroup. In such embodiments, detecting the hazard condition can include monitoring a user interface to detect manual selection of a control element of the user interface associated with each of the one or more safety mechanisms.

At step 1606, one or more safety mechanisms of a plurality of safety mechanisms are activated. In an embodiment, loss of power or the tripping of an e-stop switch (as well as other types of hazard conditions) can trigger all of the safety mechanisms to be activated, thereby shutting off fluid flow to/from the corresponding fluid lines. In other embodiments, certain hazard conditions can cause activation of only a subset of the safety mechanisms. For example, a certain hazard condition related to an occlusion can trip the safety mechanism for the patient line 130 and dialysate bag lines 126 while allowing the drain line 132 to remain open. Different combinations of safety mechanisms can be activated for different types of hazard conditions.

At step 1608, the PD machine 102 sets an alert. The alert can cause a message to be displayed on a graphical user interface of the PD machine 102 that indicates to the patient or caregiver that the safety mechanism is activated. In some cases, the alert can also cause an audible indication to sound, such as a repetitive beeping that indicates the safety mechanism is activated. The alert can cause the patient or caregiver to investigate the hazard condition and clear the issue. In some embodiments, the patient or caregiver can manually clear the alert and reset the safety mechanism. In other embodiments, the safety mechanism can be reset automatically by the PD machine 102.

At step 1610, the PD treatment cycle is reset. Once the alert has been cleared, and the safety mechanisms have been reset (e.g., deactivated), either manually or automatically, then the PD treatment cycle can resume.

Figure 17:
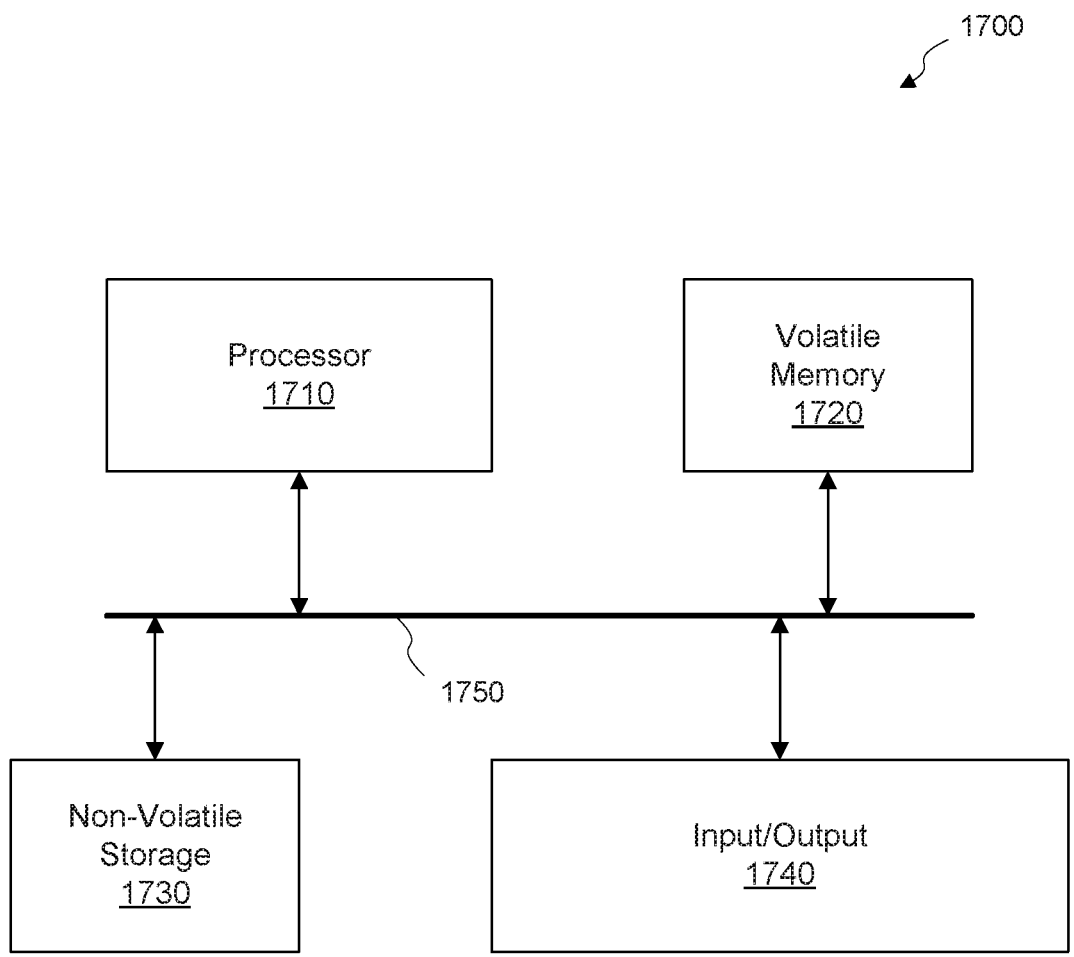
FIG. 17 illustrates an exemplary computer system, in accordance with some embodiments.

FIG. 17 illustrates an exemplary computer system 1700, in accordance with some embodiments. It will be appreciated that, in various embodiments, the control unit 139 can be implemented, at least in part, to include the components of the computer system 1700. The processor 1710 can execute instructions that cause the computer system 1700 to implement the functionality of the control unit 139, as described above. In some embodiments, the safety modules 1300/1400/1500 can also include similar components that interact with the components for the control unit 139.

As depicted in FIG. 17, the system 1700 includes a processor 1710, a volatile memory 1720, a non-volatile storage 1730, and one or more input/output (I/O) devices 1740. Each of the components 1710, 1720, 1730, and 1740 can be interconnected, for example, using a system bus 1750 to enable communications between the components. The processor 1710 is capable of processing instructions for execution within the system 1700. The processor 1710 can be a single-threaded processor, a multi-threaded processor, a vector processor that implements a single-instruction, multiple data (SIMD) architecture, a quantum processor, or the like. The processor 1710 is capable of processing instruction stored in the volatile memory 1720. In some embodiments, the volatile memory 1720 is a dynamic random access memory (DRAM). The instructions can be loaded into the volatile memory 1720 from the non-volatile storage 1730. In some embodiments, the non-volatile storage 1730 can comprise a flash memory such as an EEPROM. In other embodiments, the non-volatile storage 1730 can comprise a hard disk drive (HDD), solid state drive (SSD), or other types of non-volatile media. The processor 1710 is configured to execute the instructions, which cause the PD machine 102 to carry out the various functionality described above.

In some embodiments, the memory 1720 stores information for operation of the PD machine 102. For example, the operating parameters can be stored in the memory 1720. The processor 1710 can read the values of the operating parameters from the memory 1720 and then adjust the operation of the PD machine 102 accordingly. For example, a speed of the pistons 133A, 133B can be stored in or written to the memory 1720 and read from the memory 1720. The speed is then used to control signals transmitted to the stepper motor drivers.

The I/O device(s) 1740 provides input and/or output interfaces for the system 1700. In some embodiments, the I/O device(s) 1740 include a network interface controller (NIC) that enables the system 1700 to communicate with other devices over a network, such as a local area network (LAN) or a wide area network (WAN) such as the Internet. In some embodiments, the non-volatile storage 1730 can include both local and remote computer readable media. The remote computer readable media can refer to a network storage device such as a storage area network (SAN) or a cloud-based storage service. The I/O device(s) 1740 can also include, but are not limited to, a serial communication device (e.g., RS-232 port, USB host, etc.), a wireless interface device (e.g., a transceiver conforming to Wi-Fi or cellular communication protocols), a sensor interface controller, a video controller (e.g., a graphics card), or the like.

It will be appreciated that the system 1700 is merely one exemplary computer architecture and that the control unit 139 or other processing devices can include various modifications such as additional components in lieu of or in addition to the components shown in FIG. 17. For example, in some embodiments, the control unit 139 can be implemented as a system-on-chip (SoC) that includes a primary integrated circuit die containing one or more CPU core, one or more GPU cores, a memory management unit, analog domain logic and the like coupled to a volatile memory such as one or more SDRAM integrated circuit dies stacked on top of the primary integrated circuit dies and connected via wire bonds, micro ball arrays, and the like in a single package (e.g., chip). The chip can be included in a chipset that includes additional chips providing the I/O device 1740 functionality when connected to the SoC via a printed circuit board.

The system and techniques described herein are discussed for illustrative purposes principally in connection with a particular type of PD cycler, for example a PD cycler having piston-based pumps and a heater tray used to batch heat dialysate in a heater bag. It is noted that the system and techniques described herein may be suitably used in connection with other types and configurations of dialysis machines and/or medical devices involving the transmission of fluid to and from a patient via a patient line and for which patient line checks and occlusion detection would be beneficially performed. For example, the system and techniques described herein may be used in connection with a PD cycler using a different configuration and style of pump, such as a peristaltic pump, and may be used in connection with other types of dialysate heating arrangements, such as in-line heating arrangements. Further, the system described herein may be suitably used in connection with other types of dialysis machines, including, for example, hemodialysis machines.

It is noted that the techniques described herein may be embodied in executable instructions stored in a computer readable medium for use by or in connection with a processor-based instruction execution machine, system, apparatus, or device. It will be appreciated by those skilled in the art that, for some embodiments, various types of computer-readable media can be included for storing data. As used herein, a "computer-readable medium" includes one or more of any suitable media for storing the executable instructions of a computer program such that the instruction execution machine, system, apparatus, or device may read (or fetch) the instructions from the computer-readable medium and execute the instructions for carrying out the described embodiments. Suitable storage formats include one or more of an electronic, magnetic, optical, and electromagnetic format. A non-exhaustive list of conventional exemplary computer-readable medium includes: a portable computer diskette; a random-access memory (RAM); a read-only memory (ROM); an erasable programmable read only memory (EPROM); a flash memory device; and optical storage devices, including a portable compact disc (CD), a portable digital video disc (DVD), and the like.

It should be understood that the arrangement of components illustrated in the attached Figures are for illustrative purposes and that other arrangements are possible. For example, one or more of the elements described herein may be realized, in whole or in part, as an electronic hardware component. Other elements may be implemented in software, hardware, or a combination of software and hardware. Moreover, some or all of these other elements may be combined, some may be omitted altogether, and additional components may be added while still achieving the functionality described herein. Thus, the subject matter described herein may be embodied in many different variations, and all such variations are contemplated to be within the scope of the claims.

To facilitate an understanding of the subject matter described herein, many aspects are described in terms of sequences of actions. It will be recognized by those skilled in the art that the various actions may be performed by specialized circuits or circuitry, by program instructions being executed by one or more processors, or by a combination of both. The description herein of any sequence of actions is not intended to imply that the specific order described for performing that sequence must be followed. All methods described herein may be performed in any suitable order unless otherwise indicated herein or otherwise clearly contradicted by context.

The use of the terms "a" and "an" and "the" and similar references in the context of describing the subject matter (particularly in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. Furthermore, the foregoing description is for the purpose of illustration only, and not for the purpose of limitation, as the scope of protection sought is defined by the claims as set forth hereinafter together with any equivalents thereof. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

What is claimed is:

1. A dialysis system, comprising:
   a dialysis machine including an interface for a disposable cassette; and
   a safety module communicatively coupled to the dialysis machine via a wireless communications interface, wherein the safety module includes a plurality of safety mechanisms, wherein each safety mechanism comprises a spring attached to a compression member extendible through a corresponding opening, and wherein each safety mechanism corresponds to a particular fluid line connected to the disposable cassette,
   wherein the dialysis machine further comprises a processor configured to:
      detect a hazard condition; and
      activate one or more safety mechanisms in the plurality of safety mechanisms to isolate corresponding fluid lines connected to the disposable cassette.

2. The dialysis system of claim 1, wherein each safety mechanism operates to clamp a distensible tube of the particular fluid line to close a fluid pathway in the tube.

3. The dialysis system of claim 2, wherein at least two safety mechanisms are activated by a single actuator connected to the at least two safety mechanisms.

4. The dialysis system of claim 1, wherein the hazard condition is a loss of power.

5. The dialysis system of claim 1, wherein detecting the hazard condition comprises monitoring a user interface to detect manual selection of a control element of the user interface associated with each of the one or more safety mechanisms.

6. The dialysis system of claim 1, wherein each safety mechanism can be automatically reset by the dialysis system.

7. A method of operating a dialysis machine, the method comprising:
   detecting a hazard condition; and
   activating one or more safety mechanisms in a plurality of safety mechanisms to isolate corresponding fluid lines connected to a disposable cassette,
   wherein each safety mechanism comprises a spring attached to a compression member extendible through a corresponding opening,
   wherein the plurality of safety mechanisms are included in a safety module communicatively coupled to the dialysis machine via a wireless communications interface,
   wherein activating the one or more safety mechanisms comprises transmitting a signal to the safety module via the wireless communications interface,
   and
   wherein each safety mechanism corresponds to a particular fluid line connected to the disposable cassette in the plurality of fluid lines.

8. The method of claim 7, wherein each safety mechanism operates to clamp a distensible tube of the particular fluid line to close a fluid pathway in the tube.

9. The method of claim 7, wherein the hazard condition is a loss of power to the dialysis machine.

10. The method of claim 7, wherein detecting the hazard condition comprises monitoring a user interface to detect manual selection of a control element of the user interface associated with each of the one or more safety mechanisms.

11. A non-transitory computer readable storage medium storing instructions that, when executed by a processor, causes a dialysis machine to perform steps comprising:
   detecting a hazard condition; and
   activating one or more safety mechanisms in a plurality of safety mechanisms to isolate corresponding fluid lines connected to a disposable cassette,
   wherein the plurality of safety mechanisms are included in a safety module communicatively coupled to the dialysis machine via a wireless communications interface,
   wherein each safety mechanism comprises a spring attached to a compression member extendible through a corresponding opening,
   wherein activating the one or more safety mechanisms comprises transmitting a signal to the safety module via the communications interface,
   and wherein each safety mechanism corresponds to a particular fluid line connected to the disposable cassette in the plurality of fluid lines.

12. The non-transitory computer readable storage medium of claim 11, wherein each safety mechanism operates to clamp a distensible tube of the particular fluid line to close a fluid pathway in the tube.

\* \* \* \* \*